(12) United States Patent
Mizzen et al.

(10) Patent No.: US 7,157,089 B1
(45) Date of Patent: Jan. 2, 2007

(54) IMMUNE RESPONSES USING COMPOSITIONS CONTAINING STRESS PROTEINS

(75) Inventors: Lee Mizzen, Victoria (CA); Lawrence S. D. Anthony, Victoria (CA); Huacheng Bill Wu, Victoria (CA); Marvin Siegel, Victoria (CA)

(73) Assignee: Stressgen Biotechnologies Corporation, Victoria ( * ) Notice: Subject to any disclaimer, the term of this patent is extended or adjusted under 35 U.S.C. 154(b) by 0 days.

(21) Appl. No.: 08/977,787

(22) Filed: Nov. 25, 1997

Related U.S. Application Data

(63) Continuation-in-part of application No. 08/756,621, filed on Nov. 26, 1996, now abandoned.

(51) Int. Cl.
  *A61K 39/12* (2006.01)
  *A61K 39/295* (2006.01)
  *A61K 39/145* (2006.01)
  *A61K 45/00* (2006.01)

(52) U.S. Cl. ............... 424/192.1; 424/184.1; 424/185.1; 424/186.1; 424/201.1; 424/204.1; 424/206.1; 424/234.1; 424/281.1; 424/282.1; 530/350; 530/825; 530/826

(58) Field of Classification Search .......... 424/184.1, 424/185.1, 186.1, 192.1, 201.1, 204.1, 206.1, 424/234.1, 281.1, 282.1, 193.1, 196.11, 275.1, 424/277.1; 530/350, 825, 826
See application file for complete search history.

(56) References Cited

U.S. PATENT DOCUMENTS

| | | | |
|---|---|---|---|
| 4,716,038 A | 12/1987 | Stanford et al. ............... 424/92 |
| 4,724,144 A | 2/1988 | Rook et al. .................... 424/88 |
| 4,918,166 A | 4/1990 | Kingsman et al. ............. 530/350 |
| 5,082,767 A * | 1/1992 | Hatfield et al. ................ 435/6 |
| 5,114,844 A | 5/1992 | Cohen et al. ................. 435/7.21 |
| 5,174,993 A * | 12/1992 | Paoletti .................... 424/199.1 |
| 5,290,686 A * | 3/1994 | Kendal et al. .............. 435/69.1 |
| 5,316,910 A * | 5/1994 | Rota et al. ................... 435/7.1 |
| 5,348,945 A | 9/1994 | Berberian et al. ............ 514/21 |
| 5,504,005 A | 4/1996 | Bloom et al. ............. 435/253.1 |
| 5,578,300 A | 11/1996 | Schmidt et al. .......... 424/78.08 |
| 5,580,563 A | 12/1996 | Tam ............................ 424/197 |
| 5,599,545 A | 2/1997 | Stanford et al. .......... 424/282.1 |
| 5,690,937 A * | 11/1997 | Parkin et al. ............. 424/199.1 |
| 5,736,146 A * | 4/1998 | Cohen |
| 5,750,119 A | 5/1998 | Srivastava ................ 424/277.1 |
| 5,830,464 A | 11/1998 | Srivastava ................ 424/93.71 |
| 5,837,251 A * | 11/1998 | Srivastava |
| 5,858,368 A * | 1/1999 | Smith et al. |
| 5,935,576 A * | 8/1999 | Srivastava |
| 5,948,646 A | 9/1999 | Srivastava ................ 435/69.3 |
| 5,961,979 A | 10/1999 | Srivastava ................ 424/193.1 |
| 5,962,298 A * | 10/1999 | Fiers et al. ................. 435/201 |
| 5,985,270 A | 11/1999 | Srivastava ................ 424/93.71 |
| 5,997,873 A | 12/1999 | Srivastava ................ 424/193.1 |
| 6,007,806 A * | 12/1999 | Lathe et al. |
| 6,007,821 A | 12/1999 | Srivastava et al. ........ 424/193.1 |
| 6,017,540 A | 1/2000 | Srivastava et al. ........ 424/193.1 |
| 6,017,544 A | 1/2000 | Srivastava ................ 424/277.1 |
| 6,030,618 A | 2/2000 | Srivastava ................ 424/184.1 |
| 6,048,530 A | 4/2000 | Srivastava ................ 424/193.1 |
| 6,130,087 A | 10/2000 | Srivastava et al. ........ 435/372.3 |
| 6,136,315 A | 10/2000 | Srivastava ................ 424/193.1 |
| 6,139,841 A | 10/2000 | Srivastava ................ 424/193.1 |
| 6,143,299 A | 11/2000 | Srivastava ................ 424/193.1 |
| 6,156,302 A | 12/2000 | Srivastava ................ 424/93.1 |
| 6,162,436 A | 12/2000 | Srivastava ................ 424/193.1 |
| 6,168,793 B1 | 1/2001 | Srivastava ................ 424/193.1 |
| 6,187,312 B1 | 2/2001 | Srivastava ................ 424/193.1 |
| 6,319,503 B1 * | 11/2001 | Kenten et al. ............ 424/192.1 |
| 6,322,790 B1 | 11/2001 | Srivastava ................ 424/193.1 |
| 6,335,183 B1 | 1/2002 | Young et al. .............. 435/69.7 |
| 6,338,952 B1 | 1/2002 | Young ...................... 435/69.7 |
| 6,482,614 B1 * | 11/2002 | Young ...................... 435/69.7 |

FOREIGN PATENT DOCUMENTS

| | | |
|---|---|---|
| EP | 0 262 710 | 9/1987 |
| EP | 0 322 990 | 7/1989 |
| GB | 2 251 186 | 7/1992 |
| WO | WO 85/05034 | 11/1985 |
| WO | WO 88/00974 | 2/1988 |

(Continued)

OTHER PUBLICATIONS

Roman et al. Immunology, 1996 vol. 88 pp. 487–492.*
Suzue et al. 1996 Journal of Immunology vol. 156 pp. 873–879.*

(Continued)

*Primary Examiner*—Mary K. Zeman
(74) *Attorney, Agent, or Firm*—Fish & Richardson P.C.

(57) ABSTRACT

The present invention relates to a vaccine for inducing an immune response to an antigen in a vertebrate (e.g., mammal) comprising an antigen and all or a portion of a stress protein or all or a portion of a protein having an amino acid sequence sufficiently homologous to the amino acid sequence of the stress protein to induce the immune response against the antigen. In a particular embodiment, the present invention relates to vaccines and compositions which induce a CTL response in a mammal comprising an antigen and all or a portion of a stress protein. In another embodiment, the invention relates to vaccines and compositions which induce an immune response to an influenza virus in a mammal comprising an antigen of the influenza virus and all or a portion of one or more stress proteins. The invention also relates to vaccines and compositions for inducing a CTL response to a tumor-associated antigen comprising a tumor-associated antigen and all or a portion of the stress protein. The invention also relates to vaccines and composition for suppressing allergic immune responses to allergens comprising an allergen and all or a portion of a stress protein.

60 Claims, 9 Drawing Sheets

FOREIGN PATENT DOCUMENTS

| | | |
|---|---|---|
| WO | WO 88/05823 | 8/1988 |
| WO | WO 88/06591 | 9/1988 |
| WO | WO 89/12455 | 12/1989 |
| WO | WO 90/15873 | 12/1990 |
| WO | WO 92/08488 | 12/1990 |
| WO | WO 91/02542 | 3/1991 |
| WO | WO 91/15572 | 10/1991 |
| WO | WO 92/08484 | 5/1992 |
| WO | WO 93/17712 | 9/1993 |
| WO | WO 94/03208 | 2/1994 |
| WO | WO 94/29459 | 12/1994 |
| WO | WO 95/24923 | 9/1995 |
| WO | WO 95/31994 | 11/1995 |
| WO | WO 96/10421 | 4/1996 |
| WO | WO 96/19496 | 6/1996 |
| WO | WO 96/26277 | 8/1996 |
| WO | WO 97/06821 | 2/1997 |
| WO | WO 97/26910 | 7/1997 |
| WO | WO 99/07860 | 2/1999 |

OTHER PUBLICATIONS

Suzue, K. and Young, R.A., "Adjuvant–Free hsp 70 Fusion Protein System Elicits Humoral and Cellular Immune Responses to HIV–1 p24[1]," *J. Immunol.,* 156:873–879, (1996).

Noll, A. and Autenrieti, I.B., "Immunity against *Yersinia enterocolitica* by Vaccination with Yersinia HSP60 Immunostimulating Complexes or Yersinia HSP60 plus Interleukin–12," *Infect. & Immun.,* 64:2955–2961 (1996).

Barrios, C., et al., "Mycobacterial heat–shock proteins as carrier molecules. II: The use of the 70–kDa mycobacterial heat–shock protein as carrier for conjugated vaccines can circumvent the need for adjuvants and Bacillus Calmette Guerin priming," *Eur. J. Immunol.,* 22:1365–1372, (1992).

Kaufman, S.H.E., et al., "Enumeration of T cells reactive with *Mycobacterium tuberculosis* organisms and specific for the recombinant mycobacterial 64–kDa protein," *Eur. J. Immunol.,* 17:351–357 (1987).

Ferrero, R.L., et al., The GroES homolog of *Helicobacter pylori* confers protective immunity against mucosal infection in mice, *Proc. Natl. Acad. Sci. USA,* 92:6499–6503 (1995).

Young, D., et al., "Stress Proteins are immune targets in leprosy and tuberculosis," *Proc. Natl. Acad. Sci. USA,* 85:4267–4270 (1988).

Gomez, F. J., et al., "Vaccination with Recombinant Heat Shock Protein 60 from *Histoplasma capsulatum* Protects Mice against Pulmonary Histoplasmosis," *Infect. & Immun.,* 63:2587–2595 (1995).

Del Guidice, G., et al., "Priming to Heat Shock Proteins in Infants Vaccinated against Pertussis," *J. Immunol.,* 150(5):2025–2032 (1993).

Barrios, C. et al., Heat shock proteins as carrier molecules: in vivo helper effect mediated by *Escherichia coli* GroEL and DnaK protiens requires cross–linking with antigen, *Clin. Exp. Immunol.,* 98:229–233 (1994).

De Velasco, E.A., et al., Synthetic Peptides Representing T–Cell Epitopes Act as Carriers in Pneumococcal Polysaccharide Conjugate Vaccines, *Infect. & Immun.,* 63:961–968 (1995).

Konen–Waisman, S. et al.,"Self and Foreign 60–Kilodalton Heat Shock Protein T Cell Epitope Peptides Serve As Immunogenic Cariers for a T Cell–Independent Sugar Antigen1," *J. Immunol.,* 154:5977–5985 (1995).

Friedland, J.S., et al., "Mycobacterial 65–kD heat shock protein induces release of proinflammatory cytokines from human monocytic cells," *Clin. Exp. Immunol.,* 91:58–62 (1993).

Verdegaal, E.M.E., et al., "Heat Shock Protein 65 Induces CD62e, CD106, and CD54 on Cultured Human Endothelial Cells and Increases Their Adhesiveness for Monocytes and Granulocytes," *J. Immunol.,* 157:369–376 (1996).

Vodkin, M.H. and William, J.M., "A Heat Shock Operon in *Coxiella burnetii* Produces a Major Antigen Homologous to a Protein in both Mycobacteria and *Escherichia coli*," *J. Bact.,* 170(3):1227–1234 (1988).

Dubois, P. et al., "Protective immunization of the squirrel monkey against asexual blood stages of *Plasmodium falciparum* by use of parasite protein fractions," *Proc. Natl. Acad. Sci. USA.,* 81:229–232 (1984).

Ardeshir F., et al., "A 75 kd merozoite surface protein of *Plasmodium falciparum* which is related to the 70 kd heat–shock proteins," *EMBO J.,* 6(2):493–499 (1987).

Lamb, J.R., et al., "Stress Proteins may Provide a Link Between the Immune Response to Infection and Autoimmunity," *Int'l. Immun.,* 1(2):191–196 (1989).

Lindquist, S. and Craig, E.A., "The Heat–Shock Proteins," *Annu. Rev. Genet.,* 22:631–677 (1988).

Husson, R.N. and Young, R.A., "Genes for the major protein antigens of *Mycobacterium tuberculosis*: the etiologic agents of tuberculosis and leprosy share an immunodominant antigen," *Proc. Natl. Acad. Sci. USA,* 84:1679–1683 (1987).

Thole, J.E.R., et al., "Characterization, Sequence Determination, and Immunogenicity of a 64–Kilodalton Protein of *Mycobacterium bovis* BCG Expressed in *Escherichia coli* K–12," *Infect. Immunol.,* 55:(6):1466–1470 (1987).

Del Giudice, G., et al., "Heat shock protein as "super" – carriers for sporozoite peptide vaccines?," *Res. in Immunol.,* 162:703–707 (1991).

Young, D.B., et al., "The 65kDa antigen of mycobacterium—a common bacterial protein?," *Immunol. Today,* 8(7–8):215–219 (1987).

Young, R.A., "Stress Proteins and Immunology," Annu. Rev. Immunol., 8:401–420 (1990).

Blander, S.J. and Horwitz, M.A., "Major Cytoplasmic Membrane Protein of *Legionella pneumophila*, a Genus Common Antigen and Member of the hsp 60 Family of Heat Shock Proteins, Induces Protective Immunity ina Guinea Pig Model of Legionnaires' Disease," *J. Clin. Invest.,* 91:717–723 (1993).

Lussow, A.R., et al., "Mycobacterial heat–shock proteins as carrier molecules," Eur. J. Immunol., 21:2297–2302 (1991).

Srivastava P.K. and Udono, H., "Heat shock protein–peptide complexes in cancer immunotherapy," *Curr. Opin. Immunol.,* 6:728–732 (1994).

Levi, R. and Arnon, R., "Synthetic recombinant influenza vaccine induces efficient long–term immunity and cross–strain protection," *Vaccine,* 14(1):85–92, (1996).

DeNagel, D.C. and Pierce, S.K., "Heat shock proteins in Immune Responses," *Crit. Rev. Immunol.,* 13(1):71–81 (1993).

Agranovsky et al., "Putative 65 kDa Protein of Beet Yellows Closterovirus Is a Homologue of HSP70 Heat Shock Proteins," J. Mol. Biol., 217:603–610 (1991).

Arnosti et al., "Characterization of heat shock in *Bacillus subtilis* ," J. Bact., 168(3):1243–1249 (Dec. 1986).

Arrigo and Welch, "Characterization and Purification of the Small 28,000–Dalton Mammalian Heat Shock Protein", J. Biol. Chem., 262(32):15359–15369 (1987).

Beech et al., "CD4+ Th2 cells specific for mycobacterial 65–kilodalton heat shock protein protect against pristane–induced arthritis," J. Immunol. 159:3692–3697 (1997).

Bertelli et al., "BCG–Induced Resistance in *Trypanosoma cruzi* Experimental Infections," Tropenmed Parasitol, 32:93–96 (1981).

Birk et al., "T–cell autoimmunity in type 1 diabetes mellitus," Curr. Opin. Immunol., 5:903–909 (1993).

Blachere et al., "Heat Shock Protein–Peptide Complexes, Reconstituted in Vitro, Elicit Peptide–specific Cytotoxic T Lymphocyte Response and Tumor Immunity," J. Exp. Med. 186(8):1315–1322 (Oct. 20, 1997).

Borysiewicz et al, "A recombinant vaccinia virus encoding human papillomavirus types 16 and 18, E6 and E7 proteins as immunotherapy for cervical cancer," Lancet, 347:1523–27 (1996).

Butini et al., "Comparative Analysis of HIV–specific CTL Activity in Lymphoid Tissue and Peripheral Blood," J. Cell Biochem. Suppl. 18B Abstract J306 (1994).

Cain and Howett, "Preventing cervical cancer," Science, 288:1753–54 (2000).

Cassell et al., "A Phase II Study on the Postsurgical Management of Stage Malignant Melanoma With a Newcastle Disease Virus Oncolysate," Cancer, 52:856–860 (Sep. 1983).

Cassell et al., "Viral Oncolysate in the Management of Malignant Melanoma, I. Preparation of the Oncolysate and Measurement of Immunologic Responses" Cancer, 40:672–679 (Aug. 1977).

Catelli et al., "The common 90–kd protein component of non–transformed '8S' steroid receptors is a heat–shock protein", EMBO J., 4(12):3131–3135 (1985).

Chandrasekhar et al., "Purification and Properties of the groES Morphogenetic Protein of *Escherichia coli*", J. Biol. Chem., 261(26):12414–12419 (1986).

Cohen et al., "Immunity to 60 kDa heat shock protein in autoimmune diabetes," Diab. Nutr. Metab., 9(4):229–232 (1996).

Cohen, "Jitters jeopardize AIDS vaccine trials ," Science, 262: 980–981 (1993).

Dahlseid et al., "PBP74, a new member of the mammalian 70–kDa heat shock protein family, is a mitochondrial protein," Mol Biol Cell. 5(11):1265–1275 (1994).

de Gruijl et al., "T cell proliferative responses against human papillomavirus type 16 E7 oncoprotein are most prominent in cervical intraepithelial neoplasia patients with a persistent viral infection," Journal of General Virology, 77:2183–2191 (1996).

Del Guidice, "Hsp70: a carrier molecule with built–in adjuvanticity," Experientia, 50:1061–1066 (1994).

Doherty et al, Evasion of host immune responses by tumours and viruses, "Vaccines against virally induced cancers," Wiley, Chicester (Ciba Foundation Symposium 187), pp. 245–260. See p. 245, Abstract.

DuBois et al., "Isoltion of a Tumor–Associated Transplantation Antigen (TATA) From an SV40–Induced Sarcoma. Resemblance to the TATA of Chemically Induced Neoplasms," Int. J. Cancer. 34:561–566 (1984).

Elias et al., "Induction and therapy of autoimmune diatetes in the non–obese diabetic (NOD/Lt) mouse by a 65–kDa heat shock protein," Proc. Natl. Acad. Sci. USA, 87:1576–1580 (1990).

Falk et al., "Cell Mediated Immunity to Human Tumors," Arch. Surg., 107:261–265 (Aug. 1973).

Flaherty et al., "Three–dimensional Structure of the ATPase Fragment of a 70K Heat–Shock Cognate Protein," Nature 346:623–628.

Fox, "No Winners Against AIDS", Biotechnology, 12:128 (1994).

Galloway, "Papillomavirus oncoproteins as vaccine candidates," Lancet, 347:1498–99 (1996).

Gomes et al., "Heat shock protein synthesis during development in *Caulobacter crescentus*," J. Bact., 168(2):923–930 (Nov. 1986).

Haanen et al., "Selection of a human T helper type 1–like T cell subset by mycobacteria," J. Exp. Med., 174:583–592 (1991).

Haghbin et al., "Immunotherapy with Oral BCG and Serial Immune Evaluation in Childhood Lymphoblastic Leukemia Following Three Years of Chemotherapy," Cancer, 46:2577–2586 (Dec. 1980).

Hastie et al., "HSP27 Elevated in Mild Allergic Inflammation Protects Airway Epithelium from H2SO4 Effects," AM J. Physiol., 273 (Lung Cell. Mol. Physiol. 17):L401–L409 (1997).

Haynes, "Scientific and Social Issues of Human Immunodeficiency Virus Vaccine Development", Science, 260.1279–1286 (1993).

Hudson et al., "Active Specific Immunotherapy for Ovarian Cancer," The Lancet, 2:877–879 (Oct. 23, 1976).

Hughes et al., "A Study in Clinical Cancer Immunotherapy," Cancer, 26:269–278 (Aug. 1970).

Humphrey et al., "Adjuvant Immunotherapy for Melanoma," J. of Sur. Oncol., 25:303–305 (1984).

Hunt and Calderwood, "Characterization and Sequence of a Mouse hsp70 Gene and Its Expression in Mouse Cell Lines," Gene 87:199–204 (1990).

Huygen et al., "Spleen cell cytokine secretion in *Mycobacterium bovis* BCG–infected mice," Infection and Immunity, 60(7):2880–2886 (1992).

Jacquier–Sarlin, "Protective effects of hsp70 in inflammation," Experientia, 50(11–12):1031–1038 (1994).

Jarecki–Black et al., "The Effect of BCG–Vaccine Upon Experimental Visceral Leishmaniasis in Hampsters," Ann. Clin. Lab. Sci., 14:464–466 (1984).

Jindal, "Heat Shock Proteins: Applications in health and disease," Trends In Biotech, 14(1):17–20, 1996.

Jondal et al., "MHC Class I–Restricted CTL Responses to Exogenous Antigens," Immunity 5:295–203 (Oct. 1996).

Kaufmann et al., "Heat–shock protein 60: implications for pathogenesis of and protection against bacterial infections," Immunological Reviews, 121:67–90 (1991).

Kiessling et al., "Role of hsp60 during autoimmune and bacterial inflammation," Immunological Reviews, 121:91–111 (1991).

Kimmig and Wenk, "Suppression of Parasitaemia from *Litomosoides carinii* by Immunisation with BCG and Microfilariae," Z. Parasitenkd, 67:317–327 (1982).

La Thangue and Latchman, "A Cellular Protein Related to Heat–Shocked Protein 90 Accumulates during Herpes Simplex Virus Infection and Is Overexpressed in Transformed Cells," Experimental Cell Research, 178:169–179 (1988).

Layton et al., Induction of HIV–Specific Cytotoxic T lymphocytes In Vivo with Hybrid HIV–1 V3:Ty–Virus–Like–Particles, J. Immunology, 151(2):1097–1107 (Jul. 1993).

Leung et al., "The immunobiology of heat shock proteins," J. Investig. Allergol. Clin. Immunol., 1(1):23–30, (1991).

Li and Srivastava, "Tumor Rejection Antigen gp96/grp94 is an ATPase: Implications for Protein Folding and Antigen Presentation," The EMBO Journal, 12(8):3143–3151 (1993).

Maytin, "Heat shock proteins and molecular chaperones: implications for adaptive responses in the skin," J. Invest. Dermatol., 104:448–455 (1995).

McCulloch et al., "Recurrent Malignant Melanoma: Effect of Adjuvant Immunotherapy on Survival," Can. Med. Assoc. J., 117:33–36 (Jul. 1977).

Miller et al., "Immunotherapy in autoimmune disease," Curr. Opinion in Immun., 3:936–940 (1991).

Minowada et al., "Clinical implications of the stress response." J. Clin. Invest., 95:3–12 (1995).

Moréet al., Activation of cytotoxic T cells in vitro by recombinant gp96 fusion proteins irrespective of the 'fused' antigenic peptide sequence, Immunology Letters, 69:275–282 (1999).

Motal, "Glycosylphosphatidylinositol–linked Db does not induce an influenza–specific cytotoxic T lymphocyte response or recycle membrane–bound peptides," Eur. J. Immunol., 25:1121–1124 (1995).

Murphy and Lefford, "Host Defenses in Murine Malaria: Induction of a Protracted State of Immunity with a Formalin–Killed *Plasmodium berghei* Blood Parasite Vaccine," Infec. Immun., 22:798–803 (1978).

Murray et al., "Viral Oncolysate in the Management of Malignant Melanoma, II. Clinical Studies" Cancer, 40:680–686 (Aug. 1977).

Nadler et al., "Interaction of the Immunosupressant Deoxyspergualin with a Member of the Hsp70 Family of Heat Shock Proteins," Science, 258:484–486 (1992).

Oettgen and Old, "Chapter 6: The History of Cancer Immunotherapy." In Biologic Therapy of Cancer, De Vita, V.T., Hellman, S. and Rosenberg, S.A., eds., (London: J.B. Lippincott) pp. 98–103 (1991).

Orme et al., "Cytokine secretion by CD4 T lymphocytes acquired in response to *Mycobacterium tuberculosis* infection," J. Immunol., 151(1):518–525 (1993).

Palladino et al., "Expression of a Shared Tumor–Specific Antigen by Two Chemically Induced BALB/c Sarcomas," Cancer Research, 47:5074–5079 (Oct. 1987).

Peetermans et al., "Mycobacterial heat–shock protein 65 induces pronflammatory cytokines but does not activate human mononuclear phagocytes," Scan. J. Immunol., 39:613–716 (1994).

Pinskey et al., "Intravesical Administration of Bacillus Calmette–Guerin in Patients with Recurrent Superficial Carcinoma of the Urinary Bladder: Report of a Prospective, Randomized Train," Cancer Treat. Rep., 69:47–53 (Jan. 1985).

Polla et al., "Heat shock proteins and inflammation," Current Topics in Microbiology and Immunology, 167:93–105 (1991).

Polla et al., "Regulation and functions of stress proteins in allergy and inflammation," Clinical and Experimental Allergy, 23:548–556 (1993).

Polla et al., "Spontaneous heat shock protein synthesis by alveolar macrophages in interstitial lung disease associated with phagocytosis of eosinophils," Eur. Respir. J., 6:483–488 (1993).

Rico et al., "Characterization of the Immunostimulatory Properties of *Leishmania infantum* HSP70 by Fusion to the *Escherichia coli* Maltose–Binding Protein in Normal nu/nu BALB/c Mice," Infection and Immunity 66:347–352 (Jan. 1998).

Shinnick et al., "The Etiologic Agents of Leprosy and Tuberculosis Share an Immunoreactive protein Antigen with the Vaccine Strain *Mycobacterium bovis* BCG", Infect. and Immun., 55(8):1932–1935 (1987).

Silverstein, "The History of Immunology," In Fundamental Immunology, 2.sup.nd Edition, Paul, W.E., ed., (NY:Raven Press), pp. 21,23–24 (1989).

Sparks et al., "Immunology and Adjuvant Chemoimmunotherapy of Breast Cancer," Arch Surg. 111:1057–1062 (Oct. 1976).

Spencer et al., "Nonspecific Protection of Mice against Influenza Virus Infection by Local or Systemic Immunization with Bacille Calmette–Guerin," J. Infect, 171–175 (Aug. 1977).

Srivastava and Old, "Individually Distinct Transplantation Antigens of Chemically Induced Mouse Tumors," Immunology Today, 9:78–83 (Mar. 1988).

Srivastava and Das, "The Serologically Unique Cell Surface Antigen of Zajdela Ascitic Hepatoma is Also Its Tumor–Associated Transplantation Antigen," Int. J. Cancer, 33:417–422 (1984).

Srivastava and Maki, "Stress–Induced Proteins in Immune Response to Cancer," Curr. Top. of Microbiol. Immunol., 167:109–123 (1991).

Srivastava et al., "Tumor Rejection Antigens of Chemically Induced Sarcomas of Inbred Mice," Proc. Natl. Acad. Sci., USA, 83:3407–3411 (May 1986).

Sturrock et al., "Attempts to Induce Resistance to *Schistosoma mansoni* and *S. haematobium* in Kenyan Baboons (*Papio anubis*) Using Non–Specific Immunostimulants." Parasitology, 90:101–110 (1985).

Suto and Srivastava, "A Mechanisms for the Specitic Immunogenicity of Heat Shock Protein–Chaperoned Peptides," Science 269:1585–1588 (Sep. 15, 1995).

Suzue et al., "Heat Shock Fusion Proteins as Vehicles for Antigen Delivery Into the Major Histocompatibility Complex Class I Presentation Pathway," Proc. Natl. Acad. Sci. USA, 94:13146–13151 (Nov. 1997).

Tamura et al., "Immunotherapy of Tumors with Autologous Tumor–Derived Heat Shock Protein Preparations," Science 278:117–120 (Oct. 3, 1997).

Thole et al., "Antigenic relatedness of a strongly immunogenic 65 kDA mycobacterial protein antigen with a similarly sized ubiquitous bacterial common antigen", Microbial Pathogenesis, 4:71–83 (1988).

Udono et al., "Cellular Requirements for Tumor–Specific Immunity Elicited by Heat Shock Proteins: Tumor Rejection Antigen gp96 Primes CD8 T Cells in vivo," Proc. Natl. Acad. Sci. USA 91:3077–3081 (Apr. 1994.

Udono and Srivastava, "Heat Shock Protein 70–associated Peptides Elicit Specific Cancer Immunity," J. Exp. Med., 178:1391–1396 (Oct. 1993).

Ullrich et al., "A Mouse Tumor–Specific Transplantation Antigen is a Heat Shock–Related Protein," Proc. Natl. Acad. Sci., USA, 83:3121–3125 (May 1986).

van Eden et al., "Cloning of the mycobacterial epitope recongized by T lymphocytes in adjuvant arthritis", Nature, 331(14):171–173 (1988).

Vignola et al., "Increased expression of heat shock protein 70 on airway cells in asthma and chronic bronchitis," Am. J. Respir. Cell Mol. Biol., 13:683–691 (1995).

Voellmy et al. "Isolation and functional anlaysis of a human 70,000–dalton heat shock protein gene segment," Proc Natl Acad Sci U S A. 82(15):4949–53 (1985).

Welch et al., "Biochemical characterization of the mammalian stress proteins and identification of two stress proteins as glucose– and Ca2+–ionophore–regulated proteins," J. Biol. Chem., 258(11):7102–7111 (1983).

Welch and Feramisco, "Purification of the Major Mammalian Heat Shock Proteins", J. Biol. Chem., 257(24):14949–14959 (1982).

Welch and Feramisco, "Rapid Purification of Mammalian 70,000–Dalton Stress Proteins: Affinity of the Proteins for Nucleotides", Mol. Cell. Biol., 5(6):1229–1237 (1985).

Young et al., "Genes for the major protein antigens of the leprosy parasite mycobacterium laprae," Nature, 316:450–452 (1985).

Zhu et al., "Structural Analysis of Substrate Binding by the Molecular Chaperone DnaK," Science 272:1606–1614 (Jun. 14, 1996).

Zylicz et al., "The grpE Protein of *Escherichia coli*", J. Biol. Chem., 262(36):17437–17442 (1987).

Zylicz and Georgopoulos, "Purification and Properties of the *Escherichia coli* dnaK Replication Protein", J. Biol. Chem., 259(14):8820–8825 (1984).

Johansson et al. (J infectious disease 1990 vol. 162, pp. 800–809.)*

Lehninger. biochemistry. 1970, WORTH Publishers, Ny, Ny.*

Nagata et al. Biochem Biophys Res Comm. (1999) 261:445–451.*

Shaw et al., "New Aspects of Influenza Viruses", Clinical Microbiology Reviews 5:74–92 (1992).

* cited by examiner

```
                          SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
           (A) LENGTH: 12 amino acids
           (B) TYPE: amino acid
           (C) STRANDEDNESS: unknown
           (D) TOPOLOGY: unknown (ii) MOLECULE TYPE: peptide (xi) SEQUENCE DESCRIPTION: SEQ ID NO:1:

Val Gln Leu Ala Ser Asn Glu Asn Met Glu Thr Met
   1               5                   10

(2) INFORMATION FOR SEQ ID NO:2:

(i) SEQUENCE CHARACTERISTICS:
           (A) LENGTH: 13 amino acids
           (B) TYPE: amino acid
           (C) STRANDEDNESS: unknown
           (D) TOPOLOGY: unknown (ii) MOLECULE TYPE: peptide (xi) SEQUENCE DESCRIPTION: SEQ ID NO:2:

Cys Val Gln Ile Ala Ser Asn Glu Asn Met Glu Thr Met
   1               5                   10

(2) INFORMATION FOR SEQ ID NO:3:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "DNA"

(xi) SEQUENCE DESCRIPTION: SEQ ID NO:3:

AAAGAAGAAT TCAGGCGAAT C                                              21

(2) INFORMATION FOR SEQ ID NO:4:

(i) SEQUENCE CHARACTERISTICS:
           (A) LENGTH: 21 base pairs
```

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

GTTCCGATCA CTAGTCCCAC G                                              21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

CTGCTTGAAT TCAGCCAAGT G                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

CTGTTGACTA GTGTTTCCTC C                                              21

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:7:

Leu Pro Tyr Leu Gly Trp Leu Val Pro
1               5

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

Cys Lys Lys Lys Leu Pro Tyr Leu Gly Trp Leu Val Pro
1               5                  10
```

IMMUNE RESPONSES USING COMPOSITIONS CONTAINING STRESS PROTEINS

RELATED APPLICATIONS

This application is a Continuation-in-Part of U.S. application No. 08/756,621, filed Nov. 26, 1996, now abandoned, the entire teachings of which are incorporated herein by reference.

BACKGROUND OF THE INVENTION

The viruses causing influenza have been arbitrarily named as influenza type A, B, and C. These types define antigenically distinct viruses. Each type has several distinct subtypes. Viruses within one type are genetically compatible in the sense that cells infected with two different subtypes can assemble mixed viruses containing components from both subtypes. Influenza viruses are classified as orthomyxoviruses. The viruses form particles of between 80 and 120 nm in diameter. Influenza viruses are enveloped viruses. i.e., their outer surface is derived from host cell membrane. Inserted in and protruding from the envelope are two major viral-encoded proteins, hemagglutinin (HA) and neuraminidase (NA). Influenza viruses are negative-stranded RNA viruses, containing a genome made up of 8 RNA segments of non-messenger RNA polarity. The genomic RNA segments are assembled in RNP complexes with virus-encoded nuclear protein (NP). Following infection of a host cell, genomic RNA segments are first transcribed into RNAs with messenger RNA polarity which are later reverse-transcribed to produce genomic RNA. The transcriptase activities responsible for these steps lacks proof-reading capability. Mistakes that are made during transcription and reverse transcription are therefore not repaired, resulting in a high frequency of mutation of the viral genome. While all viral genes are subject to the same mutational process, genes for external proteins HA and NA are particularly subject to strong selection processes that drive their evolution towards mutant forms that escape immune detection in their hosts. Hosts include not only humans but also animals such as chicken, turkey, swine and horse.

Influenza has traditionally been one of the leading causes of human death. The clinical signs of the influenza are variable, ranging from asymptomatic to fatal infection. Typically, onset of illness is rapid and prostrating, and is almost invariably attended by cough, malaise, headache, and myalgia. Coryza, sore throat, and, less commonly, substernal pain also indicate that the primary site of infection is the respiratory system. Typically, however, fever and systemic symptoms predominate. Recovery typically is rapid. The severity of the disease is largely host-dependent and relates to age, physiological state and prior immunization by infection or immunization. A severe complication is pneumonia. Compromised individuals are prone to suffer secondary infections with bacterial pathogens that cause pneumonia. Most patients who die following influenza die with bacterial pneumonia. Minor antigenic variations in influenza virus types A and B occur yearly, causing regional epidemics. The yearly death rate from such yearly epidemics may approach 20,000 in the U.S. alone. At variable intervals between 10 and 30 years, global pandemics occur with death tolls far exceeding that of yearly epidemics. These pandemics are probably caused by genetic reassortment of components from human and animal influenza A viruses, resulting in new virus with a surface structure total alien to human experience. The death toll of the 1918–19 pandemic killed about 500,000 Americans. (As a general reference: Joshua Lederberg, *Encyclopedia of Microbiology*, 2(D-L):505–520, Academic Press Inc., San Diego, Calif. 92101 (1992).

Presently licensed vaccines include inactivated purified virus. The vaccines are trivalent and include representative strains of the two prevalent A subtypes, H3N2 and H1Ni, and a single type B strain. Attenuated live virus vaccines have also been used with some success, particularly in the previous Soviet Union. Subunit vaccines have been developed containing HA and NA (split flu vaccine; Connaught Lab.). These vaccines are not completely effective in providing protective immunity. It is generally accepted that influenza vaccines generate protective immunity mainly by means of inducing antibody responses to the viral surface proteins HA and NA. This may explain why the vaccines are only incompletely effective; they are susceptible to continuous antigenic variation in these surface proteins.

The search for differences between tumor cells and normal cells has led to the isolation and characterization of a number of so-called tumor-associated antigens (Henderson, R. A. and Finn, O. J. *Advances in Immunology*, 62:217–256 (1996)). These antigens are expressed by tumor cells but not at all or at least not in large amounts in fully differentiated cells. The sequences encoding these tumor antigens are either virus-derived or are normally present in the genome of the host. An example of a virus-derived tumor-associated antigen is the human papillomavirus transforming protein E7 present in most human cervical tumors. A typical host genome-derived tumor-associated antigen is gp 100, also referred to as pMel-17, that is expressed in many human melanomas. While tumor-associated antigens are known to induce a host immune response, the response is typically insufficient to be therapeutically effective. There is a need for approaches to stimulate this response.

Using monospecific cytotoxic T lymphocyte (CTL) clones, the expression of at least five tumor-associated antigens, termed A, B, C, D and E, has been identified in mouse P815 mastocytoma tumor cells. One of these antigens, termed P1A, expresses a single epitope that is recognized by CTL clones. Using a molecular approach, the gene for P1A was cloned and was found to be a nonmutated gene present in normal cells but transcribed and translated only in transformed cells (Van den Eynde et al., *J. Exp. Med.*, 173:1373 (1991)). Further, by examination of variants of P815 cells that had lost P1A antigen expression, it was possible to identify the sequence of the MHC class I ($L^d$)-restricted minimal CTL epitope of P1A (Lethe, et al., *Eur. J. Immunol.* 22:2283 (1992)).

Thus, a need exists for more effective vaccines against antigens associated with viruses and tumors.

SUMMARY OF THE INVENTION

The present invention relates to a vaccine for inducing a cell-mediated cytolytic immune response (cytolytic T cell (CTL) response) against an antigen in a mammal comprising the antigen and all or a portion of a stress protein (or heat shock protein (hsp)) or all or a portion of a protein having an amino acid sequence sufficiently homologous to the amino acid sequence of the stress protein to induce the immune response to the antigen. In one embodiment, the antigen is an antigen of the influenza virus. In another embodiment, the antigen is a tumor-associated antigen. The stress protein for use in the present invention can be, for example, a mycobacterial stress protein (e.g., hsp65, hsp71) or a protein having an amino acid sequence sufficiently homologous to the amino acid sequence of the mycobacterial stress protein to induce the immune response to the antigen in the mammal to whom it is administered. The antigen and stress protein of the vaccine of the present invention can be linked by chemical conjugation or as a fusion protein. The vaccine for inducing a cell-mediated cytolytic immune response against an antigen in a mammal can also comprise a polynucleotide which encodes and directs expression of an antigen and a stress protein sequence in the mammal. The polynucleotide can express the antigen and stress protein as a fusion protein.

The present invention also relates to a vaccine for inducing a cell mediated cytolytic immune response to an influenza virus in a mammal comprising an antigen of the influenza virus and all or a portion of a stress protein or all or a portion of a protein having an amino acid sequence sufficiently homologous to the amino acid sequence of the stress protein to induce the immune response against the antigen. In one embodiment, the present invention relates to a vaccine for inducing a cell-mediated cytolytic immune response against an antigen of an influenza virus in a mammal comprising a polynucleotide which directs expression of the antigen of the influenza virus and a stress protein in the mammal. The antigen of the influenza virus which can be used in the present invention includes, for example, hemagglutinin, nucleoprotein, neuraminidase, M1, M2, PB1, PB2, PA and a combination thereof.

In one embodiment, the vaccine for inducing an immune response to an influenza virus in a mammal is an antigen of the influenza virus conjugated to all or a portion of a stress protein or all or a portion of a protein having an amino acid sequence sufficiently homoglous to the amino acid sequence of the stress protein to induce the immune response to the antigen.

In another embodiment, the vaccine for use in inducing an immune response to an influenza virus in a mammal is a recombinant fusion protein which includes an antigen of the influenza virus fused to all or a portion of a stress protein or all or a portion of a protein having an amino acid sequence sufficiently homologous to the amino acid sequence of the stress protein to induce the immune response against the antigen.

The present invention also relates to compositions comprising a stress protein and an antigen of an influenza virus. In one embodiment, the composition is a conjugate comprising a stress protein joined with an antigen of an influenza virus. In another embodiment, the composition is a fusion protein (pET65MP/NP-B and pET65M/NP-D) comprising a stress protein fused to an antigen of the influenza virus.

The present invention also relates to use of the compositions for preventing or treating influenza virus in a mammal.

The present invention also relates to a vaccine for inducing a cell-mediated cytolytic immune response to a tumor-associated antigen in a mammal, the vaccine comprising a tumor-associated antigen linked to all or a portion of a stress protein or all or a portion of a protein having an amino acid sequence sufficiently homologous to the amino acid sequence of the stress protein to induce the immune response against the antigen. The antigen which can be used in the present invention comprises any mammalian tumor-associated antigen including those presently known in the art. It also includes fragments of these antigens that contain a CTL epitope.

In one embodiment, the vaccine for inducing a cell-mediated cytolytic immune response to a tumor-associated antigen in a mammal is a tumor-associated antigen chemically conjugated to all or a portion of a stress protein or all or a portion of a protein having an amino acid sequence sufficiently homologous to the amino acid sequence of the stress protein to induce the immune response against the antigen.

In another embodiment, the vaccine for inducing a cell-mediated cytolytic immune response to a tumor-associated antigen in a mammal is a recombinant fusion protein which includes a tumor-associated antigen and all or a portion of a stress protein or all or a portion of a protein having an amino acid sequence sufficiently homologous to the amino acid sequence of the stress protein to induce the immune response against the antigen.

In a further embodiment, the vaccine for including a cell-mediated cytolytic immune response to a tumor-associated antigen in a mammal is a polynucleotide containing in expressible form sequences encoding a tumor-associated antigen and all or a portion of a stress protein or all or a portion of a protein having an amino acid sequence sufficiently homologous to the amino acid sequence of the stress protein to induce the immune response against the antigen.

In yet another embodiment, the vaccine for inducing a cell-mediated cytolytic immune response to a tumor-associated antigen in a mammal can also be a polynucleotide encoding a recombinant fusion protein which includes a tumor-associated antigen and all or a portion of a stress protein or all or a portion of a protein having an amino acid sequence sufficiently homologous to the amino acid sequence of the stress protein to induce the immune response against the antigen.

The invention also relates to vaccines for suppressing allergic immune responses to natural or artificial antigens (allergens) in a mammal, the vaccines including an allergen and all or a portion of a stress protein or all or a protion of a protein having an amino acid sequence sufficiently homologous to the amino acid sequence of the stress protein to suppress the allergic responses. Any allergen, regardless of whether it is peptidic or not, can be used.

In one embodiment, the vaccine for suppressing allergic immune responses to natural or artificial antigens (allergens) in a mammal is an allergen chemically conjugated to all or a portion of a stress protein or all or a portion of a protein having an amino acid sequence sufficiently homologous to the amino acid sequence of the stress protein to suppress the allergic responses.

In another embodiment, the vaccine for suppressing allergic immune responses to natural or artificial antigens (allergens) in a mammal is a recombinant fusion protein which includes an allergen and all or a portion of a stress protein or all or a portion of a protein having an amino acid sequence sufficiently homologous to the amino acid sequence of the stress protein to suppress the allergic responses.

In a further embodiment, the vaccine for suppressing allergic immune responses to natural or artificial antigens (allergens) in a mammal is a polynucleotide containing in expressible form sequences encoding a peptidic allergen and all or a portion of a stress protein or all or a portion of a protein having an amino acid sequence sufficiently homologous to the amino acid sequence of the stress protein to suppress the allergic responses.

In yet another embodiment, the vaccine for suppressing allergic immune responses to natural or artificial antigens (allergens) in a mammal can also be a polynucleotide encoding a recombinant fusion protein which includes a peptidic allergen and all or a portion of a stress protein or all or a protion of a protein having an amino acid sequences sufficiently homologous to the amino acid sequence of the stress protein to suppress the allergic responses.

The present invention also pertains to a composition for suppressing a Th2 response to an antigen in a mammal comprising the antigen and all or a portion of a stress protein or all or a portion of a protein having an amino acid sequence sufficiently homologous to the amino acid sequence of the stress protein to suppress the Th2 response to the antigen. The composition can be a vaccine, conjugate or fusion protein.

DETAILED DESCRIPTION OF THE INVENTION

Figure 1:
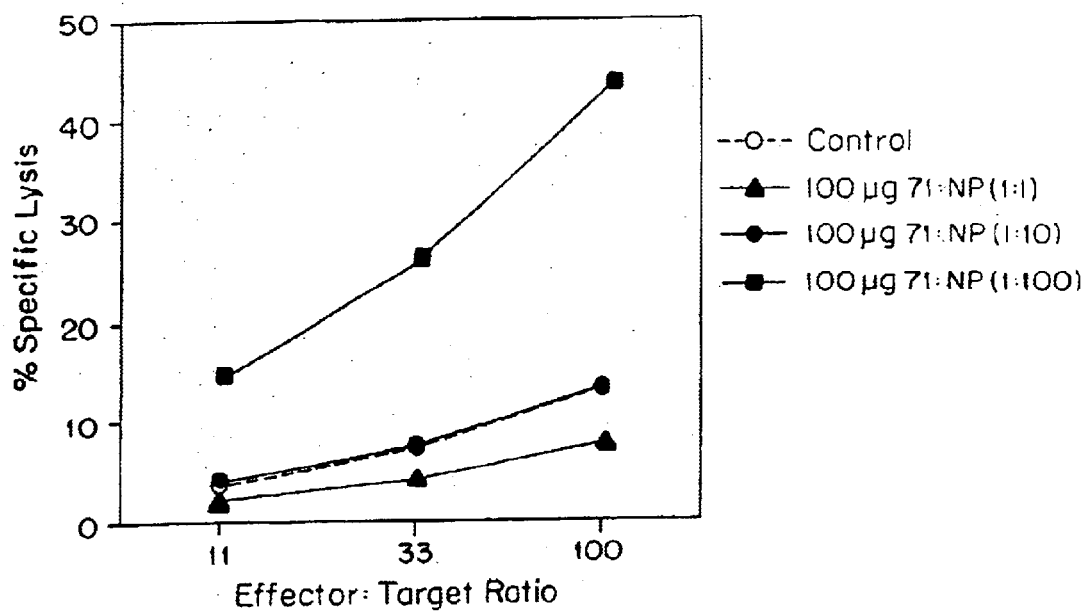
FIG. 1 is a graph of effector:target ratios versus % specific cell lysis demonstrating a cytolytic T cell (CTL) response in mice to a mixture comprising nucleoprotein (NP) peptide and heat shock protein 70 (hsp70).

The present invention relates to a vaccines and compositions which induce an immune response to an antigen in a mammal (e.g., human) comprising an antigen (one or more) and all or a portion of a stress protein or heat shock protein (one or more) or all or a portion of a protein having an amino acid sequence sufficiently homologous to the stress protein to induce the immune response against the antigen. In a particular embodiment, the present invention relates to vaccines and compositions which induce a cell mediated immune response in a mammal comprising an antigen (one or more) and all or a portion of a stress protein (one or more) or all or a portion of a protein having an amino acid sequence sufficiently homologous to the stress protein to induce the immune response against the antigen.

In a particular embodiment, the invention relates to vaccines and compositions which induce an immune response to an influenza virus in a mammal comprising an antigen of the influenza virus and all or a portion of a stress protein or all or a portion of a protein having an amino acid sequence sufficiently homologous to the amino acid sequence of the stress protein to induce the immune response against the antigen. As described herein compositions comprising an influenza antigen (e.g., NP sequences including CTL epitopes) and at least one stress protein, either in the form of mixtures of an influenza antigen and a stress protein, as a conjugate of an influenza antigen and a stress protein or as a fusion protein containing influenza antigen and stress protein sequences, are effective in stimulating specific immune responses (e.g., cytolytic T cell (CTL) response, T cell helper response, B cell response) against the influenza antigen used in mammals. For example, as demonstrated in the examples, immunization of a host (vertebrate, such as a mammal) with the vaccines described herein can result in stimulation of specific CTL activity directed against cells displaying the influenza antigen (e.g., NP). Alternatively, the individual influenza antigen and a stress protein could be administered consecutively.

In a further embodiment, the invention relates to vaccines that induce a cell-mediated immune response to tumor-associated antigens comprising a tumor-associated antigen suitable for immunization against a pre-existing tumor of a particular type or for prevention of the development of such tumor and all or a portion of a stress protein or all or a portion of a protein having an amino acid sequence sufficiently homologous to the amino acid sequence of the stress protein to induce the immune response against the antigen. Analogous to the previous embodiment, vaccines comprising at least one tumor-associated antigen and one stress protein, either in the form of mixtures of tumor-associated antigen and stress protein, conjugates of tumor-associated antigen and stress protein or fusion proteins containing tumor-associated antigen and stress protein sequences, can stimulate cell-mediated cytolytic immune responses against the tumor-associated antigen in mammals. Alternatively, the antigen and the stress protein can be administered consecutively. As demonstrated in the examples, a vaccine of this type, a fusion protein containing a minimal P1A mastocytoma antigen and a stress protein, induces a cell-mediated, cytolytic response against cells displaying the P1A antigen. Moreover, mammalian animals immunized with the vaccine are immune against a subsequent challenge with tumor cells expressing the P1A antigen.

In the present invention, the composition is comprised of two moieties: a stress protein and an antigen against which an immune response is desired. The two moieties are mixed, conjugated or joined and can form a single unit. Conjugation can be achieved by chemical means known to those skilled in the art (e.g. through a covalent bond between the stress protein and the second moiety; reductive amination) or by recombinant techniques. If recombinant techniques are used to link or connect the two moieties, the result is a recombinant fusion protein which includes the stress protein and the antigen in a single molecule. This makes it possible to produce and purify a single recombinant molecule in the vaccine production process. The stress protein can be conjugated to any antigen against which the cell mediated, cytolytic immune response is desired or to a portion of the antigen sufficient to induce an immune response in an individual to whom it is administered.

As defined herein the term "vaccine" includes compositions which can be used as a prophylactic or a therapeutic vaccine. In one embodiment, the vaccine composition is one or more nucleic acids which encode the antigen and the stress protein. The present invention also relates to use of the compositions which are nucleic acids encoding a stress protein and/or the antigen for preventing or treating a disease or condition associated with or caused by the presence of the antigen (e.g., tumor antigen), or a pathogen (e.g., bacteria, virus, parasite) which includes the antigen, in a mammal. For example, the compositions described herein can be used to induce an immune response against an influenza virus in a mammal not infected with the virus. In addition, the vaccines or compositions described herein can be used to induce an immune response against an influenza virus in a mammal infected with an influenza virus, and can result in amelioration or elimination of the disease state caused by the infecting influenza virus in the mammal. As used herein "induction of an immune response" means an increased immune response (more than undetectable or more than before); or a response that is superior to that achievable by immunization, under comparable conditions, with antigen alone.

As described herein, an antigen (one or more per stress protein) preferably is of a peptidic nature, i.e., it is a protein, polypeptide or peptide. In applications in which antigen and stress protein are admixed or chemically linked, the antigen can also be a carbohydrate, lipid, glycolipid or organic or inorganic molecule. As used herein an "antigen" includes peptides or polypeptides which comprises at least one CTL epitope. A CTL epitope is defined as either a class I-restricted T cell epitope or a class II-restricted T cell epitope. The antigen for use in the present invention can be isolated, purified (essentially pure), chemically synthesized or recombinantly produced. Other suitable antigens useful in the compositions of the present invention can be determined by those of skill in the art.

In the embodiment in which the vaccine or composition induces a cell-mediated, cytolytic immune response to an influenza virus, antigens of the influenza virus include but are not limited to hemagglutinin, whole virus, (e.g., inactivated or live, attenuated whole virus), an antigenic portion of an influenza virus and recombinantly produced virus or portions thereof. An antigen of the influenza virus includes peptides or polypeptides which comprises at least one B cell and/or T cell (e.g., T helper cell, cytolytic T cell) epitope. For example, an antigen of the influenza virus includes, but is not limited to hemagglutinin (HA, e.g., HA1, HA7), nucleoprotein (e.g., NP, such as NP-b and NP-D described in the examples), neuramidase (NA), M1, M2 PB1, PB2 and PA. Other antigens of an influenza virus which can be used in the compositions of the present invention can be determined by those of ordinary skill in the art.

In the embodiment in which the vaccine or composition induces a cell-mediated, cytolytic immune response against a tumor-associated antigen, antigens include, but are not limited to, MAGE1, MAGE3, BAGE and GAGE. These proteins are normally expressed in testis. Ectopic expression gives rise to a variety of tumors including melanomas. Also included in this list are melanocyte differentiation antigens Tyrosinase, MART-1/MELAN-1 and gp 100/pMel17 as well as tyrosinase-related protein pg75 and MUM-1, all of which are associated with melanomas. Other useful tumor-associated antigens are HER2/neu found in breast and tumors, MUC-1 found in epithelial cell tumors, and human papillomavirus proteins E6 and E7 which are associated strongly with cervical tumors. Additional antigens include GnT-V, beta-catenin, CDK4 and p15. All these tumor-associated antigens are recognized by T cells. (Wang, R.-F. and Rosenberg, S. A. *Journal of Leukocyte Biology*, 60:296–309 (1996); Houghton, A. N. *J. Exp. Med.*, 180:1–4 (1994); Henderson, R. A. and Finn, O. J., *Advances of Immunology*, 62:217–256).

The important players in allergic (atopic) and asthmatic disease are IgE and local inflammatory reactions dominated by the infiltration of eosinophils. Pulmonary hyperreactivity to nonspecific stimuli due to chronic inflammation is the modern definition of asthma. This inflammation may be cause by abnormal allergic responses to natural or artificial antigens mediated by IgE and leads to a chronic cellular infiltration of granular cells called eosinophils. The release of mediators from resident mast cells and recruited basophils and eosinophils is thought to be the cause of the inflammation and subsequent hyperreactivity. In man, as in other species, any inflammatory reaction produces local hyperreactivity. However, in asthma the inflammation is chronic, leading to life-threatening hyperreactivity unless treated appropriately. Current treatment includes the use of corticosteroids to reduce the inflammation and bronchodilators such as albuterol (beta agonists) for prompt symptomatic relief.

In humans as in mice, two distinct patterns of cytokine secretion have been defined among $CD4^-$ helper T cell clones (del Prete, G., *Allergy*, 47:450–455 (1992)). Human type 1 helper (Th1) but not type 2 helper (TH2) cells produce interleukin-2 (IL-2), gamma interferon and tumor necrosis factor beta. Th2 cells but not Th1 cells secrete IL-4 and IL-5 but not IL-2 or gamma interferon. Other cytokines such as IL-3, IL6, GM-CSF or tumor necrosis factor alpha are produced by both Th1 and Th2 cells. The different cytokine patterns are associated with different functions. In general, Th2 cells provide an excellent helper function for B cell antibody production, particularly of the IgE class. Th1 cells are responsible for delayed hypersensitivity reactions and are cytolytic for autologous antigen presenting cells including B cells. Most allergen- or helminth-antigen specific human $CD4^+$ T cell clones exhibit a Th2 phenotype while most clones specific for bacterial antigens show a Th1 profile. Allergen specific Th2 cells seem to play a crucial role in atopy. These cells induce IgE production via IL-4 and favor the proliferation, differentiation and activation of eosinophils via IL-5. In addition, Th2 derived IL-3, IL-4 and IL-13 are mast cell growth factors that act in synergy, at least in vitro. There is evidence that allergen-specific Th2 cells are selectively enriched in tissues affected by allergic inflammation such as the bronchial mucosa of humans with allergic asthma.

With the increasing use of antibiotics in early childhood in the developed world, the incidence of and deaths due to (allergic) asthma are rising. The following discussion is using this information that links increased incidence and severity of allergic reactions to a lack of exposure and T cell memory for bacterial proteins including stress proteins to support the notion that deliberate exposure to bacterial antigens including stress proteins will dampen allergic responses.

Many scientists believe that the development of resistance or sensitivity to environmental antigens depends on the nature of immunological memory generated during early antigen encounters in infancy and early childhood (Holt P. G., *Toxicol Lett.*, 86:205–201). This process appears to be antigen driven. Selection is for specific Th1 versus Th2 like memory cells within individual immune responses to inhaled antigens, a process which occurs in the regional lymph nodes draining the conducting airways. This selections appears to be regulated by a variety of cytokines produced by antigen specific $CD4^+$ and $CD8^+$ T cells. This T cell selection process can theoretically be influenced by infectious agents: infections in the airway mucosa may mobilize and activate local tissue (alveolar) macrophages which migrate to the regional lymph nodes and secrete Th2 inhibitory cytokines such as IL-12 and alpha-interferon. In addition, they may add to the gamma-interferon levels in the milieu through activation of natural killer cells. The net result is the production of CTLs (which are predominantly $CD8^+$ cells). Gamma-interferon inhibits the generation of Th2 cells and therefore production of IL-4 and IL-5, cytokines crucial for the generation of humoral (IgE) and cellular (eosinophils, basophils and mast cells) allergic responses (Anderson, G. P. and Coyle, A. J., *Trends Pharmacol. Sci.,* 15:324–332 (1995); Stam, W. B., van Oosterhout, A. J. and Nijkamp, F. P., *Life Sci.,* 53:1921–1934 (19939)).

In mammals, stress proteins have been shown to induce humoral as well as cellular immune responses. As shown in the examples herein, when soluble antigen mixed with, chemically conjugated to or fused to a stress protein is administered a mammal, cell-mediated cytolytic immune responses are substantially enhanced. These responses are largely due to $CD8^+$ T cells. Therefore, a comparison of the $CD4^+$ responses to antigens by themselves to those mixed with or coupled to stress proteins give the predicted profile: soluble antigens mixed with or linked to stress proteins yield a high proportion of CTLs (mainly $CD8^+$ T cells) which are a measure of stimulation of the Th1 pathway described before because these CTLs arose as a result of the induction of antigen specific T cells of the Th1 type. These Th1 cells produce gamma-interferon, which cytokine inhibits Th2 cells. Therefore, the Th2 cytokines IL-4 and IL-5 are no longer available to support the production of IgE and eosinophils. With decreasing titer of IgE, direct antigenic stimulation of mast and basophil cells will decline. In addition, decreased IL-5 production will lead to decreased production, differentiation and activation of eosinophils. This pattern will cause decreased inflammation of the involved tissue and result in less hyperreactive (asthmatic) events.

Therefore, administration of mixtures of known allergenic antigens (allergens) and stress proteins or compositions containing allergens chemically linked to or fused to stress proteins should influence the Th1 to Th2 ratio in atopic patients, restoring a more normal balance and leading to decreased allergy or asthma. Stress proteins used in such compositions are preferably of bacterial of mycoplasmic origin. Allergens used in allergen-stress protein fusion proteins are necessarily of a peptidic nature; nonpeptidic allergens can be used in conjugates containing an allergen and a stress protein or a mixtures of allergen and stress protein. Nonlimiting examples for allergens include Fel d 1 (cat); Amb a 1 (antigen E), Amb a 2 (antigen K) (ragweed); Der f 2, Der p 1, Der p 9, Der t 1 (mites); Bla g 1, Bla g 2 (cockroach); Bet v 1 (birch); Rat n 1 (rat); Cha o 1 (Japanese cypress); Hev b 5 (latex); gp40 (mountain cedar). For a reasonably comprehensive list of allergens up to the time of publication, see King, T. P. et al., *Int. Arch. Allergy Immunol.,* 105:224–233 (1994).

When compositions containing covalently linked or admixed allergen and stress protein are administered by a suitable route such as subcutaneous or intramuscular injection or even given by inhalation to a patient in need of treatment for hypersensitivity reactions, they should produce a decrease in allergic symptoms as measured by the classic hyperreactivity test in asthma, for example. After treatment, the patient will exhibit less nonspecific reactivity. In asthmatics, or in animal models of asthma, hyperreactivity is measured by determining the doses of inhaled methacholine that induce a bronochoconstrictive response. Mammals with chronic inflammatory conditions which lead to hyperreactivity will exhibit greater sensitivity to methacoline challenge. They will bronchoconstrict at lower doses than "normal" mammals. After treatment with the appropriate stress protein-containing composition, the dose response to methacholine would shift to less sensitive.

Any suitable stress protein (heat shock protein (hsp)) can be used in the compositions of the present invention. For example, as described in the example, hsp65 and/or hsp71 can be used. Turning to stress proteins generally, cells respond to a stressor (typically heat shock treatment) by increasing the expression of a group of genes commonly referred to as stress, or heat shock, genes. Heat shock treatment involves exposure of cells or organisms to temperatures that are one to several degrees Celsius above the temperature to which the cells are adapted. In coordination with the induction of such genes, the levels of corresponding stress proteins increase in stressed cells. As used herein, a "stress protein," also known as a "heat shock protein" or "Hsp," is a protein that is encoded by a stress gene, and is therefore typically produced in significantly greater amounts upon the contact or exposure of the stressor to the organism. A "stress gene", also known as "heat shock gene" is used herein as a gene that is activated or otherwise detectably unregulated due to the contact or exposure of an organism (containing the gene) to a stressor, such as heat shock or glucose deprivation or addition. "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise. In addition to the increased expression of the Hsps, the cell downregulates certain other genes, activates several kinases involved in signal transduction, changes the intracellular locale of certain proteins, and, in some situations, can experience changes at the cytosekeletal level as well as transient growth arrest.

In particular embodiments, the stress proteins for use in the present invention are isolated stress proteins, which means that the stress proteins have been selected and separated from the host cell in which they were produced. Such isolation can be carried out as described herein and using routine methods of protein isolation known in the art. (Maniatis et al., *Molecular Cloning, A Laboratory Manual,* Cold Spring Harbor Laboratory, Cold Spring Harbor, N.Y., 1982; Sambrook et al., *Molecular Cloning: A Laboratory Manual,* 2d Ed., Cold Spring Harbor Laboratory Press, 1989)). The isolated stress protein may also, further, be purified (essentially pure) in accordance with the methods, particularly the detergent purification methods.

In bacteria, the predominant stress proteins are proteins with molecular sizes of about 70 and 60 kDa, respectively, that are referred to as Hsp70 and Hsp60, respectively. These and other specific stress proteins and the genes encoding them are discussed further below. In bacteria, Hsp70 and Hsp60 typically represent about 1–3% of cell protein based on the staining pattern using sodium dodecyl sulfate polyacrylamide gel electrophoresis and the stain coomassie blue, but accumulate to levels as high as 25% under stressful conditions. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the preexposure of cells to mildly stressful conditions that induce the synthesis of stress proteins affords protection to the cells from the deleterious effects of a subsequent more extreme stress.

The major stress proteins appear to be expressed in every organism and tissue type examined so far. Also, it appears that stress proteins represent the most highly conserved group of proteins identified to date. For example, when stress proteins in widely diverse organisms are compared, Hsp90 and Hsp70 exhibit 50% or higher identity at the amino acid level and share many similarities at nonidentical positions.

The genes encoding stress proteins may be present in a single copy or in multiple, non-identical copies in the genome of a cell or organism. For example, the human genome has been shown to contain at least one copy of an Hsp100 gene, at least two different Hsp90 genes, up to ten Hsp70 genes of which at least several are non-identical copies, several T complex genes (Tcp genes) and at least one gene encoding the related mitochondrial protein Hsp60, as well as at least three copies of small Hsp genes encoding proteins in the 20–30 kDa range of molecular size. In most groups of stress genes there is at least one gene whose expression level is relatively high and is either entirely constitutive or only mildly heat shock-inducible. Furthermore, several groups of stress genes include members that are not up-regulated by heat but by other cues such as increased calcium levels, etc.

The stress proteins, particularly Hsp70, Hsp60, Hsp20-30 and Hsp10, are among the major determinants recognized by the host immune system in the immune response to infection by *Mycobacterium tuberculosis* and *Mycobacterium leprae*. Young, R. A., and Elliott, T. J., Stress Proteins, Infection, And Immune Surveillance, *Cell* 50:5–8, (1988). Further, some rat arthritogenic T-cells recognize Hsp60 epitopes. Van Eden, W., Thole, J., van der Zee, R., Noordzij, A., van Embden, J., Hensen, E., and Choen, I., *Nature* 331:171–173, (1988). However, individuals, including healthy individuals, with no history of mycobacterial infection or autoimmune disease also carry T-cells that recognize both bacterial and human Hsp60 epitopes; a considerable fraction of T-cells in healthy individuals that are characterized by expression of the gamma-delta T-cell receptor recognize both self and foreign stress proteins. O'Brien, R., Happ, M., Dallas, A., Palmer, E. Kubo, R., and Born, W., *Cell* 57:664–674 (1989). Thus, individuals, even healthy individuals possess T-cell populations that recognize both foreign and self stress protein epitopes.

This system of recognizing stress protein epitopes constitutes an "early defense system" against invading organisms. The system may be maintained by frequent stimulation by bacteria and viruses that cause the host cells to upregulate their own stress genes. However, the presence of autoreactive T-cells is compatible with normal health and does not cause antiimmune disease; this also demonstrates the safety of stress proteins within an individual. The safety of stress proteins is additionally demonstrated by the success and relative safety of BCG (Bacille Calmette Guerin, a strain of *Mycobacterium bovis*) vaccinations, which induce an immune response against stress proteins that is also protective against *Mycobacteriurn tuberculosis*.

Stress genes and proteins for use in the present invention are those well known in the art and include, for example, Hsp100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases. Marcario, A. J. L., Cold Spring Harbor Laboratory Res. 25:59–70, 1995; Parsell, D. A., & Lindquist, S., *Ann. Rev. Genet.* 27:437–496 (1993); U.S. Pat. No. 5,232,833 (Sanders et al.). A particular group of stress proteins includes Hsp90, Hsp70, Hsp60, Hsp20-30, and ubiquitin, further preferably Hsp70 and Hsp60.

A stress protein in the methods and compositions of the present invention is preferably selected from extracellularly antigen-presenting stress proteins or from stress proteins that are processed and the resulting peptide fragments are presented on the surface of the cell, such that it is an extracellularly antigen-presenting protein. Additionally, a selected stress gene or protein for use in the present invention is preferably selected such that the stress gene or protein is unregulated pursuant to one or more forms of stress in at least one expression, preferably a bacterium or a human. Further preferably, the selected stress genes or proteins are unregulated in humans, including by stressors such as those described above or transformation.

Hsp100-200 examples include Grp170 (for glucose-regulated protein), Grp170 resides in the lumen of the ER, in the pre-golgi compartment, and may play a role in immunoglobulin folding and assembly.

Hsp100 examples include mammalian Hsp110, yeast Hsp 104, c1pA, c1pB, c1pC, c1pX and c1pY. Yeast Hsp104 and *E. coli* c1pA, form hexameric and *E. coli* c1pB, tetrameric particles whose assembly appears to require adenine nucleotide binding. C1p protease provides a 750 kDa heterooligomer composed of C1pP (a proteolytic subunit) and of C1pA. C1pB-Y are structurally related to a C1pA, although unlike C1pA they do not appear to complex with C1pP.

Hsp90 examples include HtpG in *E. coli,* Hsp83 and Hsc83 yeast, and Hsp90α, Hsp90β and Grp94 in humans. Hsp90 binds groups of proteins, which proteins are typically cellular regulatory molecules such as steroid hormone receptors (e.g., glucocorticoids, estrogen, progesterone, and testosterone), transcription factors and protein kinases that play a role in signal transduction mechanisms. Hsp90 proteins also participate in the formation of large, abundant protein complexes that include other stress proteins.

Lon is a tetrameric protein functioning as an ATP-dependent protease degrading non-native proteins in *E. coli*.

Hsp70 examples include Hsp72 and Hsp73 from mammalian cells, DnaK from bacteria, particularly mycobacteria such as *Mycobacterium leprae, Mycobacterium tuberculosis,* and *Mycobacterium bovis* (such as Bacille-Calmette Guerin), DnaK from *Escherichia coli,* yeast, and other prokaryotes, and BiP and Grp78.

Hsp70 is capable of specifically binding ATP as well as unfolded polypeptides and peptides, thereby participating in protein folding and unfolding as well as in the assembly and disassembly of protein complexes.

Hsp60 examples include Hsp65 from mycobacteria. Bacterial Hsp60 also commonly known as GroEL, such as the GroEL from *E. coli*. Hsp60 forms large homooligomeric complexes, and appears to play a key role in protein folding. Hsp60 homologues are present in eukaroytic mitochondria and chloroplasts.

TF55 examples include Tcp1, TRiC and thermosome. The proteins are typically occur in the cytoplasm of eukaryotes and some archaebacteria, and form multi-membered rings, promoting protein folding. They are also weakly homologous to Hsp60.

Hsp40 examples include DnaJ from prokaryotes such as *E. coli,* and mycobacteria and HSJ1, HDJ1 and Hsp40. Hsp40 plays a role as a molecular chaperone in protein synthesis, thermotolerance and DNA replication, among other cellular activities.

FKPBs examples include FKBP12, FKBP13, FKBP25, and FKBP59, Fpr1 and Nep1. The proteins typically have peptidyl-prolyl isomerase activity and interact with immunosuppressants such as FK506 and rapamycin. The proteins are typically found in the cytoplasm and the endoplasmic reticulum.

Cyclophilin examples include cyclophilins A, B and C. The proteins have peptidyl-prolyl isomerase activity and interact with the immunosuppressant cyclosporin A. The protein cyclosporin A binds calcineurin (a protein phosphatase). Hsp20-30 examples include α-crystallin, and Hsp20-30 is also referred to as small Hsp. Hsp20-30 is typically found in large homooligomeric complexes or, possibly, also heterooligomeric complexes where an organism or cell type expresses several different types of small Hsps. Hsp20-30 interacts with cytoskeletal structures, and may play a regulatory role in the polymerization//depolymerization of actin. Hsp20-30 is rapidly phosphorylated upon stress or exposure of resting cells to growth factors.

C1pP is an *E. coli* protease involved in degradation of abnormal proteins. Homologues of C1pP are found in chloroplasts. C1pP forms a heterooligomeric complex with C1pA.

GrpE is an *E. coli* protein of about 20 kDa that is involved in both the rescue of stress-damaged proteins as well as the degradation of damaged proteins. GrpE plays a role in the regulation of stress gene expression in *E. coli.* Hsp10 examples include GroES and Cpn10. Hsp10 is typically found in *E. coli* and in mitochondria and chloroplasts of eukaryotic cells. Hsp10 forms a seven-membered ring that associates with Hsp60 oligomers. Hsp10 is also involved in protein folding.

Ubiquitin has been found to bind proteins in coordination with the proteolytic removal of the proteins by ATP-dependent cytosolic proteases.

In particular embodiments, the stress proteins of the present invention are obtained from enterobacteria, mycobacteria (particularly *M. leprea. M. tuberculosis* and *M. bovis, E. coli,* yeast, Drospholia, vertebrates, avians, chickens, mammals, rats, mice, primates, or humans.

The stress proteins may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the mutant. Due to code degeneracy, for example, there may be considerable variation in nucleotide sequences encoding the same amino acid sequence. The present invention is also suitable for use with stress protein fragments or peptides obtained from stress proteins, provided such fragments or peptides include the conformational epitopes involved with enhancing the immune response to the chosen antigen. Stress protein fragments may be obtained by fragmentation using proteinases, or by recombinant methods, such as the expression of a portion of a stress protein-encoding nucleotide sequence (either alone or as fusions with another protein). Peptides may also be produced by such methods, or by chemical synthesis. The present invention is also suitable for use with a stress protein fused or conjugated to a second protein, which may or may not be a stress protein. The stress proteins may include mutations introduced at particular loci by a variety of known techniques. See, e.g., Sambrook et al., *Molecular Cloning: 4 Laboratory Manual,* 2d Ed., Cold Spring Harbor Laboratory Press, 1989; Drinkwater and Klinedinst, *PNAS* 83:3402–3406, 1986; Liao and Wise *Gene* 88:107–111, 1990'); Horwitz et al., *Genome* 3:112–117, 1989.

The term "sufficiently homologous to the amino acid sequence of the stress protein" means that the amino acid sequence of the protein or polypeptide will generally show at least 40% identity with the stress protein amino acid sequence; in some cases, the amino acid sequence of a functional equivalent exhibits approximately 50% identity with the amino acid sequence of the stress protein.

Methods of identifying a gene or a protein under consideration as a stress gene or protein are well known in the art. For example, the conservation of the genes and proteins of a particular stress protein group permits comparison of the nucleotide or amino acid sequence of the gene/protein under consideration with well known stress genes such as DnaK, GroEL or DnaJ, e.g., by nucleic acid hybridization or nucleic acid or amino acid sequencing followed by computer comparison analysis. Voellmy, R., et al., *PNAS* 82:4949–4953 (1985). Alternatively, an assay may be used to identify and/or discriminate between essential structural features and/or functional properties of a selected stress protein. For example, an expression library may be screened using anti-Hsp antibodies and other assays well known in the art. *Antibodies: A Laboratory Manual,* Harlow and Lane (eds.), Cold Spring Harbor Laboratory Press, (1988). In addition, the biological activity of a given stress protein group may be exploited. Guidon, P. T., and Hightower, L. E., *Biochem.,* 25:3231–3239 (1986). For example, Hsp70 is capable of specifically binding ATP as well as unfolded polypeptides and peptides in the assembly of protein complexes. Thus, mixing a protein under consideration with a sample comprising appropriate polypeptides, peptides, or ATP, followed by determination of the presence or absence of production of protein-protein or protein-nucleic acid complexes indicates the apparent presence or absence of an Hsp70 gene or protein, which presence or absence can be confirmed utilizing other assays such as antibody-based assays.

An effective dosage of the stress proteins of the present invention as vaccines, to elicit specific cellular and humoral immunity to stress proteins, or to substances conjugated to the stress proteins, such as proteins or oligoscaccharides, is in the range of 0.1 to 1000 ug hsp per injection, depending on the individual to whom the stress protein is being administered (Lussow, A. R., et al., *Eur. J. Immun.,* 21:2297–2302 (1991); Barrios, C. et al., *Eur. J. Immun.,* 22:1365–1372 (1992)). The appropriate dosage of the stress protein for each individual will be determined by taking into consideration, for example, the particular stress protein being administered, the type of individual to whom the stress protein is being administered, the age and size of the individual, the condition being treated or prevented and the severity of the condition. Those skilled in the art will be able to determine using no more than routine experimentation, the appropriate dosage to administer to an individual.

The stress protein, stress protein portion, stress protein functional equivalent and the antigen to which the stress protein is admixed, fused or conjugated, present in the vaccine can be produced or obtained using known techniques. For example, the stress protein and/or the antigen of influenza virus can be obtained (isolated) from a source in which it occurs in nature, can be produced by cloning and expressing a gene encoding the desired stress protein or the antigen or can be synthesized chemically or mechanically.

The compositions described herein can be used to induce an immune response against a variety of pathogens (e.g., bacteria, virus, parasite). The composition comprising an antigen of the influenza virus and all or a portion of one or more stress proteins or all or a portion of a portion having an amino acid sequence sufficiently homologous to the amino acid sequence of the stress protein to induce the immune response against the antigen can be used to induce an immune response to an influenza virus in any vertebrate (e.g., mammals, fowl) susceptible to an influenza virus. For example, the compositions can be used to induce an immune response against an influenza virus in primates (e.g., humans), horses, swine, turkeys and chickens.

The compositions described herein can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compositions described herein can be administered together with other components or biologically active agents (e.g., alum), pharmaceutically acceptable surfactants (e.g., glycerides), excipients (e.g., lactose), carriers, diluents and vehicles.

Further, the stress protein and/or peptidic antigen can be administered by in vivo expression of polynucleotides encoding such into a mammalian subject. That is, a vector can be used to deliver nucleic acid(s) encoding an antigen and a stress protein or a nucleic acid encoding a fusion protein containing antigen and stress protein sequences. For example, the stress protein and/or the antigen can be administered to host (mammal) using live vectors wherein the live vectors containing stress protein and antigen nucleic acid sequences are administered under conditions in which the antigen and/or the stress protein are expressed in vivo. For example, a mammal can be injected with a vector which encodes and expresses an antigen in vivo in combination with a stress protein in protein or peptide form, or in combination with a vector which codes for and expresses a stress protein in vivo. Alternatively, a host can be injected with a vector which encodes and expresses stress protein in vivo in combination with an antigen in peptide or protein form, or in combination with a vector which encodes and expresses an antigen in vivo. A single vector containing the sequences encoding a protein (peptide) antigen can also be used for the compositions of the present invention.

Several expression vector systems are available commercially or can be reproduced according to recombinant DNA and cell culture techniques. For example, vector systems such as the yeast or vaccinia virus expression systems, or virus vectors can be used in the methods and compositions of the present invention (Kaufman, R. J., *A J. of Method. in Cell and Molec. Biol.*, 2:221–236 (1990)). Other techniques using naked plasmids or DNA, and cloned genes encapsidated in targeted liposomes or in erythrocytes ghosts, can be used to introduce the stress protein and/or antigen polynucleotides into the host (Freidman, T., *Science*, 244:1275–1281 (199); Rabinovich, N. R., et al., *Science*, 265:1401–1404 (1994)). The construction of expression vectors and the transfer of vectors and nucleic acids into various host cells can be accomplished using genetic engineering techniques, as described in manuals like *Molecular Cloning and Current Protocols in Molecular Biology*, which are hereby incorporated by reference, or by using commercially available kits (Sambrook, J., et al., *Molecular Cloning*, Cold Spring Harbor Press, 1989; Ausubel, F. M., et al., *Current Protocols in Molecular Biology*, Greene Publishing Associates and Wiley-Interscience, 1989)).

The amount of stress protein and/or antigen in the compositions of the present invention is an amount which produces an effective immunostimulatory response in the host (vertebrate such as mammal). An effective amount is an amount such that when administered, it results in an enhanced immune response relative to the immune response when not administered. That is, an effective amount is an amount that provides a more pronounced immune response than similar amounts of the antigen or the stress proteins alone. In addition, the amount of stress protein and/or antigen administered to the host will vary depending on a variety of factors, including the antigen employed, the size, age, body weight, general health, sex, and diet of the host, and the time of administration, duration or particular qualities of the influenza virus. Adjustment and manipulation of established dose ranges are well within the ability of those skilled in the art. For example, the amount of stress protein and antigen can be from about 100 ug to about 1 g, preferably about 1 mg to about 1 g, and from about 1 mg to about 100 mg.

The present invention teaches that the presence of a stress protein greatly stimulates the cell-mediated cytolytic response to an antigen. Although tumor-associated antigens have been identified, the immune responses against these antigens alone are not therapeutically effective. Enhancement of the cellular response against these antigens by means of co-administration of a stress protein, either in a mixture or linked to antigen, is beneficial in cancer therapy. This expectation is supported by the observation detailed in the examples that a composition of the present invention immunizes a mammalian animal against a subsequent tumor challenge. Enhancement of the cell-mediated, cytolytic response against an antigen is predicted to result in the downregulation of a preexisting (Th2-mediated) humoral response against the same antigen. The present invention is therefore also useful for suppressing allergic responses. Finally, T cell-mediated immunity is also considered to be an important element in the mammalian host's defense against infections caused by viruses, protozoa and certain intracellular bacteria such as mycobacteria. As is shown in the examples, compositions (mixtures, conjugates and fusion proteins) of the present invention including a stress protein and an influenza virus antigen are effective in eliciting a substantial cell-mediated cytolytic response against mammalian cells expressing the viral antigen.

The present invention is illustrated by the following examples, which are not intended to be limiting in any way.

EXAMPLES

Example 1

Isolation of Recombinant Stress Proteins

A. Recombinant Mycobacterial Hsp70.

Plasmid Y3111 contains an *M. tuberculosis* Hsp70 gene functionally inserted between expression control sequences. (Mehlert, A. and Young, D. B., *Mol. Microbiol.*, 3:125–130 (1989). *E. coli* strain CG2027 (obtained from C. Georgopoulos, University of Geneva, Switzerland) containing a truncated Hsp70 gene was transformed with plasmid Y3111 by standard procedures. (Maniatis, et al., *Molecular Cloning, A Laboratory Manual*, Cold Spring Harbor Laboratory, Cold Spring Harbor, N.Y. (1982)).

Bacteria containing plasmid Y3111 were grown overnight in 2×YT medium (20 g Tryptone, 10 g yeast extract, 10 g NaCl per liter) containing 100 microgram/ml ampicillin at 37° C., with agitation (250 rpm). A 10% glycerol stock was prepared from this culture and was stored at −70° C. Several scrapings from the frozen glycerol stock were used to inoculate a large culture that was incubated as before for about 48 h. When the optical density at 590 nm reached 2.5 to 3.5, cells were collected by centrifugation.

The following steps were performed at 4° C. Cell pellets were resuspended in 3 ml per gram of lysis buffer. The composition of lysis buffer was 10 mM Tris-HCl, 2 mM ethylenediamine tetraacetate (EDTA), 5 mM beta-mercaptoethanol, 10 microgram/ml aprotinin, 10 microgram/ml leupeptin, and 1 microgram/ml pepstatin. Lysozyme was added to the cell suspension to a final concentration of 0.14 mg/ml. The suspension was then frozen at −70° C.

The cell suspension was thawed, and cells were broken by sonication. Sonicates were subjected to centrifugation at 17,000 rpm for 30 min. (JA-17 rotor, Beckman). Solid $(NH_4)_2SO4$ was added to the supernatant solution until that solution was 65% saturated with $(NH_4)_2SO4$. After a 30 min. inubation, the mixture was centrifuged as before. The pellet was dissolved in Q SEPHAROSE buffer A. To this soltuion were added 10 microgram/ml aprotinin, 10 microgram/ml leupeptin, and 1 microgram/ml pepstatin, and the solution was dialyzed overnight against 65 volumes of Q SEPHAROSE buffer A. Q SEPHAROSE buffer A contained 30 mM Tris-Hcl (pH 7.5), 1 mM EDTA, 5 mM beta-mercaptoethanol. The dialyzed solution was clarified by centrifugation as described above.

Dialyzed solution was applied to a Q SEPHAROSE column (Pharmacia) equilibrated in Q SEPHAROSE buffer A. The column was washed with 2 volumes of the same buffer. Elution was with a 0 to 600 mM NaCl gradient. Fractions were tested by SDS-PAGE and staining with Coomassie Blue for the presence of a major 71 kDa polypeptide (i.e., the recombinant *M. tuberculosis* Hsp70 protein). Fractions containing the polypeptide were pooled, and the pool was brought to 65% saturation by the addition of solid $(NH_4)_2SO4$. The mixture was centrifuged as described before, the pellet was dissolved in ATP Start buffer (50 mM Tris-HCl (pH 8.0), 20 mM NaCl, 5 mM $MgCl_2$, 15 mM beta-mercaptoethanol and 0.1 mM EDTA), and the resulting protein solution dialyzed overnight against 65 volumes of the same buffer and clarified by centrifugation.

The dialyzed protein solution was then applied to an ATP-agarose column (Fluka) equilibrated in ATP Start buffer. The column was washed with 1 column volume of ATP Start buffer with 1 M NaCl. Elution was achieved with ATP Start buffer supplemented with 10 mM ATP. The eluate was brought to 65% saturation with $(NH_4)_2SO4$, and precipitated protein was collected as described before. The centrifugation pellet was dissolved in and diazlyzed against 200 volumes of Blue SEPHAROSE buffer (30 mM Tris-HCl (pH 7.5), 5 mM $MgCl_2$, 5 mM beta-mercaptoethanol).

The dialyzed protein solution from the last step was applied to a Blue SEPHAROSE column (Pharmacia) equilibrated Blue SEPHAROSE buffer. The column was washed with 1.5 column volumes of the same buffer. The flow-through and was fractions were collected as a single pool.

The purity of the final preparation was assessed by SDS-PAGE and Coomassie Blue staining, by western blot analysis (Maniatis, et al., *Molecular Cloning, A Laboratory manual,* Cold Spring Harbor Laboratory, Cold Spring Harbor, N.Y. (1982); (see Sambrook et al., *Molecular Cloning: A Laboratory manual,* $2^{nd}$ ed., Cold Spring Harbor Laboratory press, NY (1989)) using mouse monoclonal antibodies specific for mycobacterial Hsp70 and *E. coli* Hsp70, respectively, and by assays of ATPase activity. Preparations are typically more than 90% pure based on the staining pattern of the preparation in coomassie blue stained gels, and preferably more than 95% pure, and contained less than 1% of *E. coli* Hsp60 and no detectable *E. coli* Hsp70.

B. Mycobacterial Hsp60

Plasmid RIB1300 contains an *M. bovis* BCG Hsp60 gene functionally inserted between expression control sequences. (Thole, J. E. R., et al., *J. Exp. Med.,* 178:343–348 (1993). *E. coli* strain M1546 was transformed with plasmid RIB1300 (Thole, J. E. R., et al., supra.) using standard procedures. Maniatis, et al., *Molecular Cloning, A Laboratory Manual,* Cold Spring Harbor laboratory, Cold Spring Habor, N.Y. (1982).

An inoculum of bacteria containing plasmid RIB1300 was grown to saturation in NCZYM medium (10 g N-Z Amine A, 5 g Bacto yeast extract, 1 g Casamino acids, 5 g NaCl, 2 g $(NH_4)_2SO_4$-$7H_2O$) per liter) containing 200 microgram/ml of ampicillin at 28° C. and under agitation. This culture was used to inoculate a larger culture which was grown under the same conditions as the inoculum culture until the optical density of the culture was between 0.3 to 0.6 at an optical density of 590 nm. Production of the recombinant protein was initiated by rapidly raising the temperature of the culture to 42° C. by incubation in a hot water bath. The culture was maintained at this temperature for 3 h. The bacteria were then collected by centrifugation and resuspended in 6 volumes per weight of bacterial pellet of lysis buffer. Lysis buffer contained 10 mM Tris-JCL (pH 8.0), 10 mM ethylenediamine tetraacetate (EDTA), 0.1 mM PMSF and 0.1% RIVM BA (0.104 g 4-amino-benzamidine-2HCl, 0.066 g epsilon-amino acaproic acid per 50 ml). Lysozyme was added to a concentration of 0.1 mg/ml, and the suspension was frozen at −70° C.

The bacterial suspension was thawed and placed at 4° C. The following operations were at this temperature. Complete lysis of bacteria was achieved by sonication. The sonicate was centrifuged at 17,000 rpm for 30 min in a JA-17 rotor (Beckman). Saturated $(NH_4)_2SO_4$ was added to the supernatant solution until 20% saturation wa achieved. Precipitates were removed by centrifugation (see above) and were discarded. The supernatant solution was brought to 55% saturation by the addition of saturated $(NH_4)_2SO_4$. The pellet resulting from the subsequent centrifugation was dissolved in TE buffer (10 mM Tris-HCl (pH 8.0), 15 mM beta-mercaptoethanol, 1 mM EDTA). The protein solution in TE was then dialyzed against 50 volumes of TE buffer.

After centrifugation (as above) to remove precipitated material, the dialyzed protein solution was applied to a DEAS SEPHAROSE (Pharmacia) column. After washing with TE buffer, proteins were eluted with a 0–300 mM NaCl gradient in TE buffer. Fractions containing an *M. bovis* BCG Hsp60 (actual apparent molecular weight equal to 65 kDa), were identified by SDS-PAGE and Coomassie Blue staining and were pooled. 10 microgram/ml aprotinin, 10 microgram/ml leupeptin, and 1 microgram/ml pepstatin were added to the pool which was then concentrated in an Amicon cell using a YM30 membrane.

The concentrated pool was applied to a S-200 SEPHACRYL (Pharmacia) column equilibrated with S200 buffer (10 mM $Na_2HPO_4$ (pH 6.8), 150 mM NaCl and 15 mM beta-mercaptoethanol). Elution was with the same buffer. Fractions were tested for the presence of mycobacterial Hsp60 as before, and positive fractions containing highly purified protein were pooled and dialyzed overnight against HAP buffer (10 mM, Na$_2$HPO$_4$ (pH 6.8), 15 mM beta-mercaptoethanol).

The dialyzed pool was applied to a hydroxyapatite (Bio-Rad; Bio-Gel HTP Gel) column equilibrated in HAP buffer. The column was washed with 3 column volumes of 1 mN MgCl$_2$ and 15 mM beta-mercaptoethanol and then with 1 mM Na$_2$HPO$_4$ (pH 6.8) and 15 mM beta-mercaptoethanol. Protein was eluted with a 10–60 mM phosphate gradient. Fractions were tested as before, and positive fractions were pooled, concentrated and exchanged into 0.85% NaCl by means of gel filtration through PD10. The purity of mycobacterial Hsp60 was assessed by SDS-PAGE and Coomassie Blue staining as well as by western blot analysis using antibodies specific for E. coli Hsp70 and Hsp60. Preparations were typically more than 90% pure, and contained no more than 0.5% of E. coli Hsp60 and 0.1–0.2% E. coli Hsp70, respectively.

Hsp preparations can be depyrogenated either by affinity chromatography on DetoxiGel resin, addition of polymyxin B or (least preferably) by extraction with detergents such as Triton X-114.

Example 2

CTL Response to a Composition Comprising a Mixture of an NP Peptide and hsp70 a. Preparation of hsp70 and NP peptide

Hsp 70, here *M. tuberculosis* hsp71, was prepared as described in example 1. NP peptide (referred to herein as NP.B; Motal, U.M.A., et al., *Eur. J. Immunol.*, 25:1121–1124 (1995) and references therein) with the amino acid sequences VQLASNENMETM (SEQ ID NO: 1) corresponding to residues 363–374 in the complete NP and containing a known CTL epitope (H-2b-restricted) was produced synthetically (0.25 mM scale) on an Applied Biosystems model 431A peptide synthesizer using Fmoc (9-fluorenylmethyloxycarbonyl) as the alpha-amino protective group and HMP (Wang) resin as the solid support. All amino acid and synthesis chemicals were purchased from Applied biosystems.

NP.B was cleaved off the support and side-chain-protecting groups were removed by incubating under continuous agitation NP.B-resin for 3 h in 2 ml of a mixture prepared by combining 10 ml trifluoroacetic acid, 0.5 ml water, 0.75 g crystalline phenol, 0.25 ml ethanedithiol and 0.5 ml thioanisole. The cleavage mixture was filtered into 40 ml of ice cold diethyl ether. Insoluble material was collected by centrifugation at 5000×g for 8 min. Ether was decanted and the pellet washed three times by resuspension in cold diethyl ether followed by centrifugation. After the last wash the pellet was air-dried, taken up in distilled water and lyophilized.

b. Immunization of mice and preparation of effector cells

NP.B peptide was dissolved in a small volume of Dulbecco's PBS (DPBS; 2.7 mM KH2PO$_4$, 4.3 mM Na$_2$HPO$_4$, 2.7 mM KCl, 0.137 M NaCl). 1.89, 18.9 or 189 microgram aliquots, respectively, of peptide NP.B were mixed with 100 microgram aliquots of hsp71 in DPBS to obtain compositions with molar ratios of peptide:hsp of 1, 10, or 100, respectively. Groups of four female mice of strain C57BL/6 were either left unimmunized (control) or were injected subcutaneously in the nape of the neck with the three different NP.B-hsp71 mixtures. After seven days, the mice were euthanized by cervical dislocation, and their spleens were removed. Single cell suspensions of pooled spleens were prepared and washed once in 'complete medium', which was RPMI-1640 medium supplemented with 10% fetal bovine serum, 2 mM L-glutamine, 1 mM sodium pyruvate, 50 uM 2-mercaptoethanol and 50 ug/ml gentamycin sulfate. Lymphoid cells were restimulated by culturing 25×10$^6$ viable cells with NP.B peptide at a 0.1 unmolar concentration for five days. Cultures were incubated in upright 25 cm2 flasks with 10 ml complete medium at 37° C. and 5% CO2. The cultures (effector cells) were then used in the CTL activity assay described below.

c. CTL activity assay

EL4 cells (H-2b) were used as target cells. Cells were incubated for 90 min with 150 uCi Na$_2$CrO$_4$ and 10 ug NP.B peptide per 10$^6$ cells. Following extensive washing to remove excess radiolabel, 10$^4$ labeled target cells were co-cultured with restimulated effector cells at various effector:target cell ratios. After 4–5 hours of incubation, culture plates were centrifuged for 5 min at 200×g, and 100 ul aliquots of supernatant solutions containing radiolabel released from cells were collected into Beckman Ready Caps. Radioactivity was measured by liquid scintillation counting. To determine spontaneously released and total releasable radioactivity, supernatant solutions from cultures containing target cells only or from target cells lysed by the addition of Triton X-100 were collected, and radioactivity determined as before. Results were expressed as % specific lysis, calculated based on the following formula:

Percent Specific lysis=
100×(cpmtest−cpmspont/(cpmtotol−cpmspont), wherein cmptest is the radioactivity released from a particular co-culture, cpmspont is the spontaneously released radioactivity of target cell culture and cpmtotal is the radioactivity released by Triton X-100 lysis of target cells. CTL assays were performed in triplicate, and averaged value were provided.

Results of the experiment are shown in FIG. 1. The control reaction, i.e., assay of chromium release of a co-culture of target cells and effector cells prepared from unimmunized mice, provides a background value for lysis of about 10% at an effector:target cell ratio of 100. No enhancement of CTL activity over background was observed with effector cells from mice immunized with 1:1 or 10:1 NP.B-hsp71 mixture. Greatly enhanced lysis was found with effector cells from mice immunized with a 100:1 mixture of NP.B peptide and hsp71, demonstrating that co-immunization with a peptide such as NP.B and an hsp such as hsp71 can drastically stimulate CTL activity against cells displaying the peptide. Note that, as is well known in the field, immunization with NP.B peptide in DPBS alone does not stimulate CTL activity.

Example 3

CTL Response to a Composition Comprising a Chemical Conjugate of an NP Peptide and hsp70 a. Preparation of hsp70 and NP peptide

M. Tuberculosis hsp71 was prepared as described in Example 1. NP.B peptide was synthesized as discussed in Example 2, except that the peptide contained an extra amino-terminal cysteine residue and, thus, had the amino acid sequence CVQIASNENMETM (SEQ ID NO: 2).

b. Chemical conjugation of Np.B peptide to hsp70 and diphtheria toxoid

Conjugations were carried out with both hsp70 and, to provide a standard for comparisons of efficacies of specific stimulation of CTL activity, commonly used carrier protein diphtheria toxoid (abbreviated DT; DT was obtained from a commercial source).

b.1 Activation of M. tuberculosis hsp71 and DT carrier proteins

Nine mg of hsp71 were dissolved in 4.5 ml of 0.1 M sodium borate buffer, pH 8.0. Sulfo-MBS (m-maleimidobenzoyl-N-hydroxysulfosuccinimide ester) (2.3 mg in 100 ul dimethyl sulfoxamine) was added to the protein, and the reaction mixture was incubated for 1 hour at room temperature. The pH was then adjusted to 6.0, and the reaction mixture dialyzed overnight at 4° C. against 1 liter of 20 mM sodium phosphate and 150 mM NaCl, pH 5.6. DT was similarly treated.

b.2. Preparation of NP.B peptide for conjugation

For each conjugation reaction, 3 mg of peptide was dissolved in 100 ul of 0.1 M beta-mercaptoethanol. After 1 hour of incubation to allow reduction of the peptide, reducing agent was removed by drying the reaction mixture in a SpeedVac centrifuge. Peptide was redissolved in 0.5 ml distilled water to which 5 ul aliquots of 1 N NaOH were added until the peptide was fully dissolved. For conjugation experiments with DT, 6 mg of peptide were reduced and then redissolved in 1 ml of water.

B.3. Conjugate formation

The pH of the activated carrier protein solutions was adjusted to 6.8 using 0.1 N NaOH. Solution containing 3 mg of activated carrier protein was reacted with 0.5 ml of reduced peptide solution (or 1 ml of reduced peptide solution for the preparation of conjugates with DT) for 3 hours at room temperature with continuous mixing. To remove unreacted peptide, the resulting conjugate-containing solution was dialyzed overnight at 4° C. against 1 liter of 20 mM sodium phosphate and 150 mM NaCl, pH7. Protein concentration was determined by BCA assay. The efficiency of conjugation achieved by this procedure had been determined in prior pilot experiments using radiolabeled NP.B peptide. The peptide:protein ratio was found to be 17.5 for NP.B-hsp71 conjugate (71.NP) and 10.1 for NP.B-DT (DT-NP).

c. Immunization of mice and preparation of effector cells

Immunizations with 1–100 ug of 71.NP and DT.NP conjugates and preparation of effector cells were performed as described in Example 2.

d. CTL activity assay

Assay were performed as described in Example 2.

Results

Figure 2:
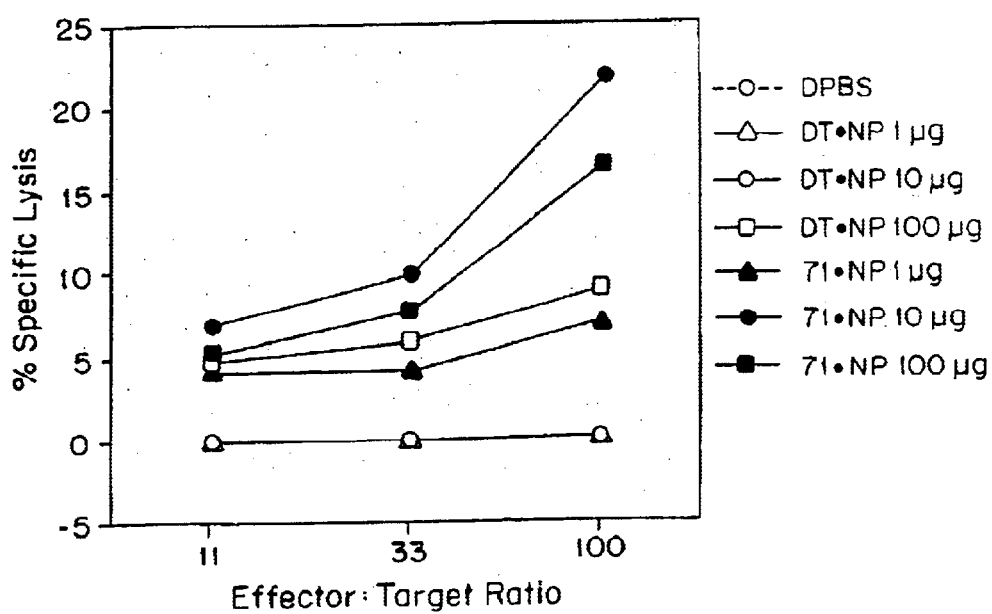
FIG. 2 is a graph of effector:target ratio versus % specific cell lysis demonstrating a CTL response in mice to a composition comprising a chemical conjugate of an NP peptide and hsp70.

Results obtained are displayed in FIG. 2. CTL activity assays with effector cells from mice injection with DPBS or with 1 or 10 ug of DT.NP conjugate gave negative results (lowest line FIG. 2). Only effector cells injected with 100 ug of DT.NP produced measurable (between 5 and 10% lysis at an effector: target cell ratio of 100) CTL activity that was comparable to that of effector cells from mice immunized with 1 ug of 71.NP. Assays with effector cells from mice immunized with 10 or 100 ug of 71.NP conjugate showed substantially greater CTL activity i.e., between 15 and 25% target cell lysis at an effector:target cell ratio of 100. This experiment demonstrates on the example of the NP.B peptide and hsp71 that immunization with a peptide-hsp conjugate stimulates specific CTL activity directed against cells displaying the peptide.

Example 4

CTL Response to a Composition Comprising an hsp-NP Fusion Protein a. Preparation of hsp-NP fusion proteins a.1. Preparation of expression plasmids encoding fusion proteins containing NP CTL epitopes at the carboxy terminus of mycobacterial hsp65

Plasmids expressing as part of hsp65 fusion proteins influenza virus NP sequences including the H-2b CTL epitope NP.B (see above) or the H-2$^J$ CTL epitope NP.D (residues 147–155 of NP; Levi, R. and Arnon, R., *Vaccines,* 14:85–92 (1996) and references therein) were constructed.

Figure 3:
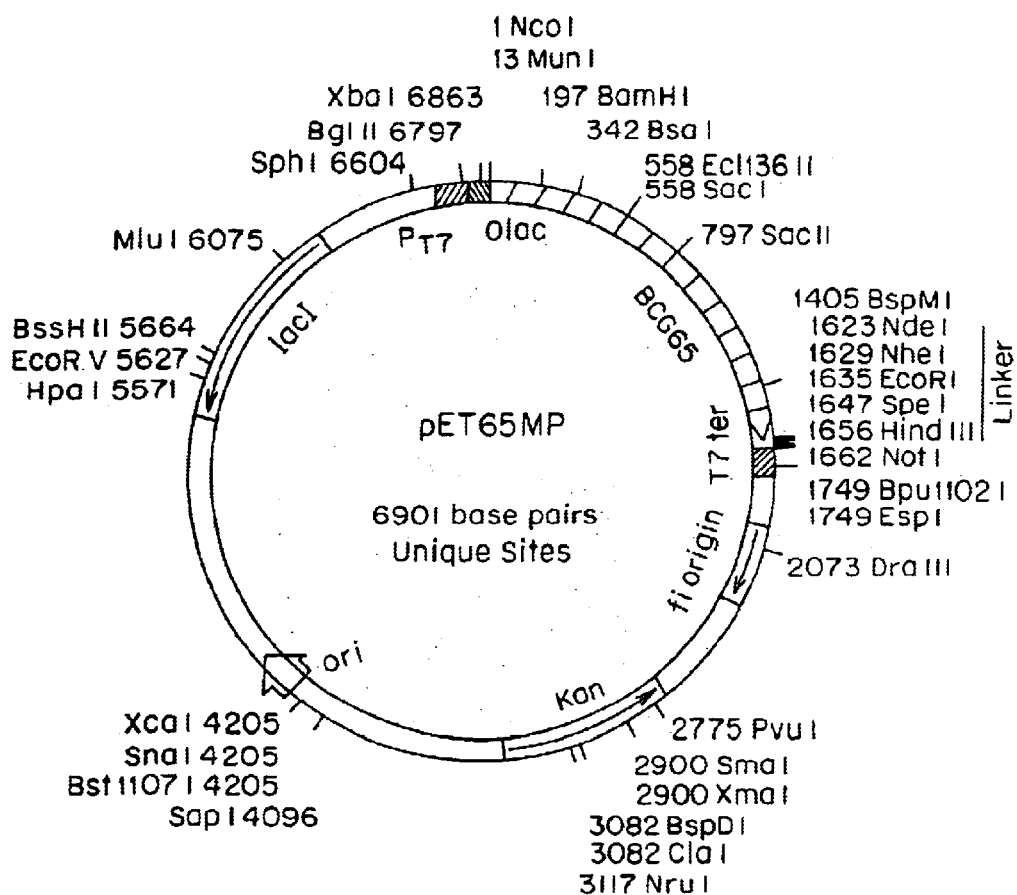
FIG. 3 is a schematic representation of the vector, pET65MP.

An expression vector, pET65mp, derived from a pET system plasmid (Novagen) and containing a complete *M. bovis* BCG hsp65 gene and useful restriction sites for insertion of additional coding sequences at the carboxy terminus of the hsp65 gene was previously constructed. A schematic representation of this vector is provided in FIG. 3.

Construct pNP/cA containing the open reading frame of NP of influenza virus strain A/PR/8/34 under the control of the cytomegalovirus promoter provided by plasmid pcDNA1 (Invitrogen) was obtained from Dr. Peter Palese (Dept. Of Microbiology, Mount Sinai School of Medicine, New York, N.Y.).

Two primer pairs for amplification of fragments containing the NP.B and NP.D epitopes were synthesized on an automated oligonucleotide synthesizer and were purified using routine procedures. Forward primers contained, in addition to appropriate sequences complementary to NP sequences, an EcoRI restriction site, and reverse primers a SpeI restriction site. The forward primer for the NP.D fragment had the sequence 5' AAAGAAGAATTCAGGC-GAATC (SEQ ID NO: 3), and the reverse primer the sequence 5' GTTCCGATCACTAGTCCCACG (SEQ ID NO: 4). This pair was designed to amplify a fragment containing NP residues 117–200. The forward primer for the NP.B fragment had the sequence 5' CTGCTTGAAT-TCAGCCAAGTG (SEQ ID NO: 5), and the reverse primer the sequence 5'CTGTTGACTAGTGTTTCCTCC (SEQ ID NO: 6). The latter pair was designed to produce a fragment containing NP residues 310–395.

Figure 4A:
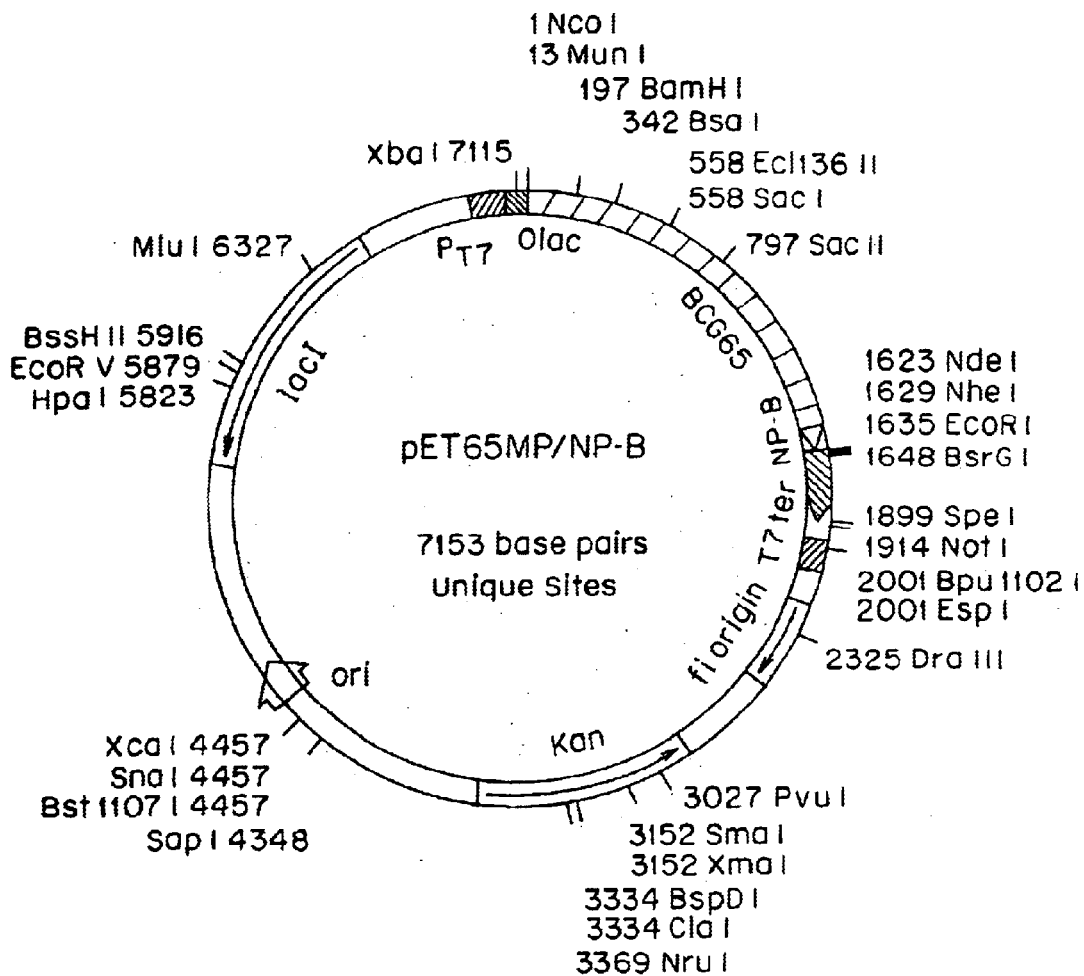
FIG. 4A is a schematic representation of the vector, pET65MP/NP-B.
Figure 4B:
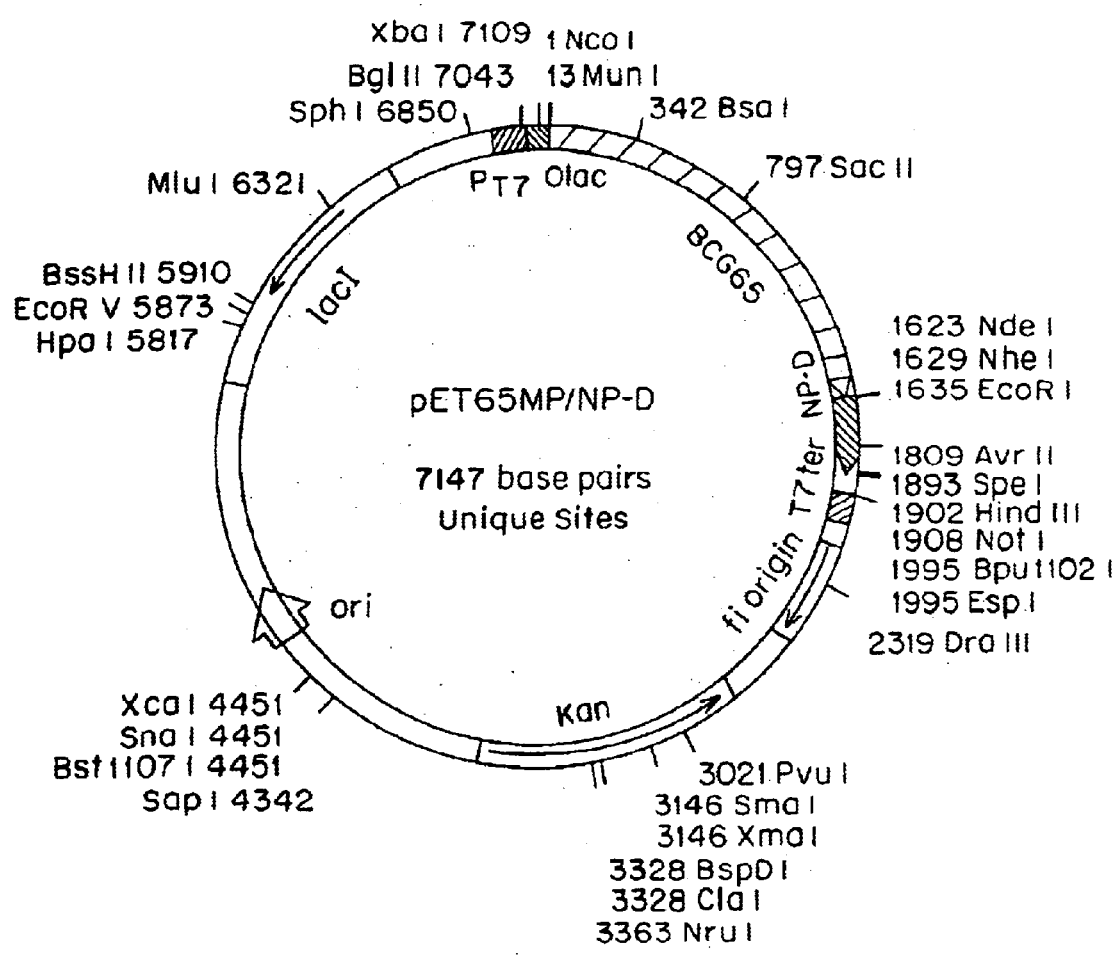
FIG. 4B is a schematic representation of the vector, pET65MP/NP-D.

Polymerase chain reactions (PCR) were carried out using the above primer pairs and pNP/cA as the DNA template. PCR fragments were double-digested with restricted endonucleases EcoRI and SpeI and ligated to EcoRI/SpeI-cut pET65mp using routine subcloning procedures (Maniatis et al., *Molecular Cloning, A Laboratory Manual,* Cold Spring Harbor Lab., Cold Spring Harbor, N.Y. (1988)). Transformation-competent cells of *E. coli* strain DH5alpha were transformed with the ligation mixture and plated out on agar containing 100 ug/ml ampicillin. Colonies of transformed cells were isolated, and plasmid DNA prepared and analyzed for the presence of the correct hsp65-NP.B or D fusion gene sequence by restriction mapping and nucleotide sequencing. Correct constructs encoding hsp65-NP.B (pET65mp/B) and hsp65-NP.D (pET65mp/D) fusion proteins were identified and were used in subsequent manipulations aimed at expression of fusion proteins in bacteria and their purification. See FIGS. 4A–4B for schematic representations of the fusion protein gene constructs, pET65MP/NP-B and pET65MP/NP-D, respectively.

a.2. Expression and purification of hsp65-NP fusion proteins

Fusion protein constructs were transformed into *E. coli* strain BL21 (DE3; Novagen), and fusion proteins were expressed in 6 liter cultures of the latter strain, using a protocol closely similar to the supplier's suggested protocol. Cells were harvested by centrifugation, suspended in 10 mM Tris-Hcl, 2 mM EDTA, and 5 mM beta-mercaptoethanol, pH 7.5 and lysed by sonication. After removing insoluble material by centrifugation, ammonium sulfate was added to 20% saturation, and precipitation proteins were collected by centrifugation. The presence of fusion protein in the ammonium sulfate pellet was verified by SDS-PAGE followed by Coomassie blue staining. The same assay was used to monitor all subsequent purification steps. Protein was redissolved in 30 mM Tris-Hcl, 2 mM EDTA and 5 mM beta-mercaptoethanol, pH 7.5, and the solution was exhaustively dialyzed against the same buffer before being applied to a DEAE Sepharose (fast flow, Pharmacia Biotech) column equilibrated in the same buffer. The flow-through fraction (unbound protein) was collected which typically contained about 90 mg of protein. To further purify hsp65-NP.B fusion protein, 60 mg of the latter fraction was dialyzed against 10 mM sodium phosphate, pH 6.8 and then applied to a hydroxyapatite (BIORAD) column equilibrated in the same buffer. Elution was performed using a 0–600 mM potassium phosphate gradient. This procedure resulted in the recovery of only about 5 mg protein. The column was then further eluted with 4 M guanidinium hydrochloride which removed another 15 mg of protein. The fractions were dialyzed against DPBS and concentrated using an Amicon ultrafiltration device, before being applied to a Detoxiel column for flow-through depyrogenation. To further purify hsp65-NP.D fusion protein, DEAE Sepharose flow-through fraction was dialyzed against 30 mM sodium acetate, 2 mM EDTA, and 5 mM beta-mercaptoethanol, pH 5.8–7.5 and then applied to an SP Sepharose (fast flow, Pharmacia Biotech) column equilibrated in the same buffer. Elution was with a 0–600 mM NaCl gradient. Eluted hsp65-NP.D fusion protein was processed as described for hsp65-NP.B fusion protein. Fusion proteins purified by these procedures were more than 90% pure as estimated from stained SDS-PAGE gels and were substantially pyrogen-free.

b. Immunization of mice and preparation of effector cells

Immunizations with DPBS (referred to in FIGS. 5 & 6 as 0 ug 65-NP) or 1–100 of hsp65-NP.B or hsp65-NP.D fusion proteins and preparation of effector cells were performed essentially as described in Example 2, except that C57BL/6 mice were used in experiments with hsp65-NP.B, and BALB/c mice in experiments with hsp65-NP.D. In vitro restimulation was carried out over a period of seven days, either in the absence or in the presence of 3U/ml of recombinant human IL2 (to generally stimulate T cell proliferation).

c. CTL assays

Assays were performed essentially as described in Example 2, except that EL4 (H-2b) target cells were used in experiments with hsp65-NP.B fusion protein and P815 (H-2$^d$) target cells in experiments with hsp65-NP.D fusion protein. To provide an additional control for the specificity of the CTL response, target cells were either pulsed with the appropriate NP peptide (closed symbols in FIGS. 5A–5B & 6A–6B), were pulsed with the irrelevant residue 49-to-57-peptide derived from the sequence of the HPV16E7 protein (open symbols in FIGS. 5A–5B) or were not pulsed (open symbols in FIGS. 6A–6B).

Figure 5A:
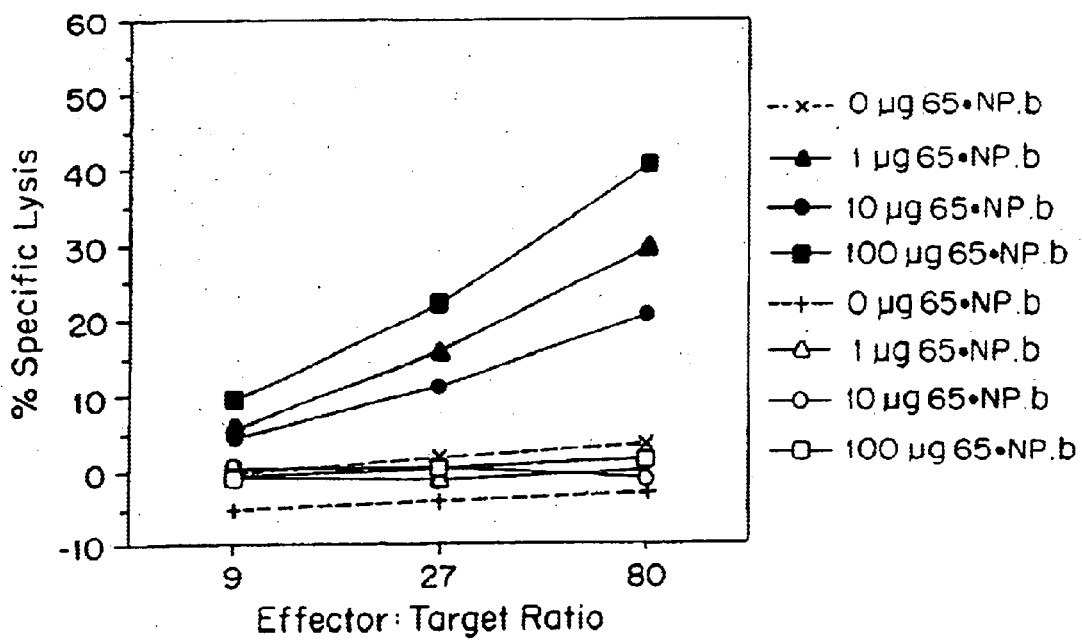
FIGS. 5A–5B are graphs of effector:target ratio versus % specific cell lysis demonstrating a CTL response in mice to the hsp-NP fusion protein, hsp65-NP.B, wherein the effector cells were restimulated in the absence of IL-2 (FIG. 5A) and in the presence of IL-2 (FIG. 5B).
Figure 5B:
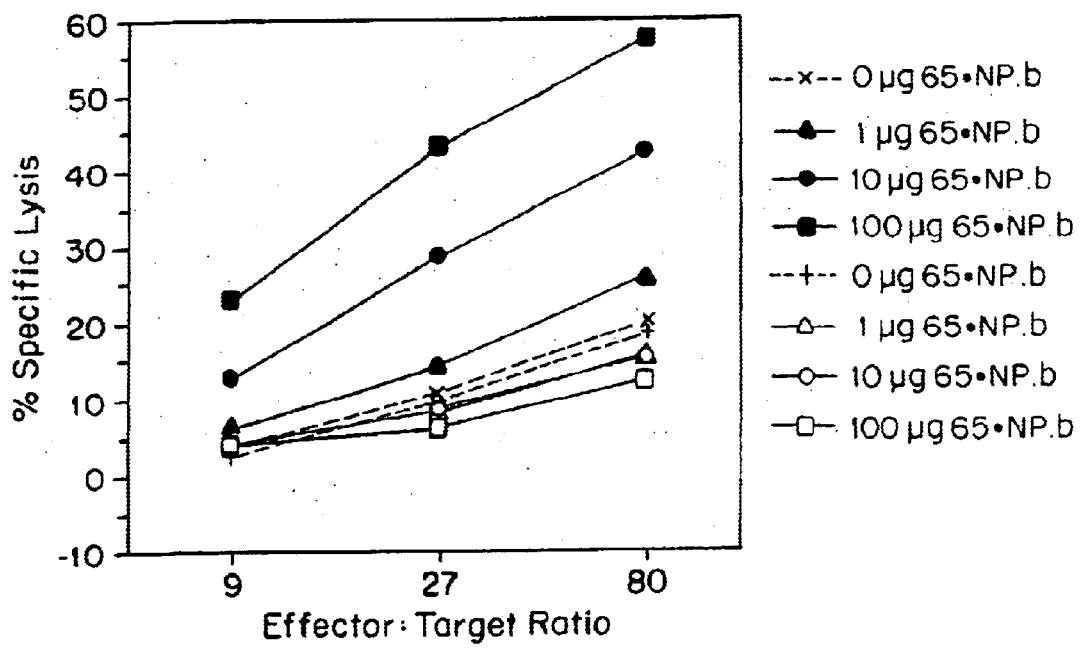

The results of experiments with hsp65-NP.B fusion protein (labeled 65-P.b) are shown in FIGS. 5A–5B. FIG. 5A refers to an experiment in which effector cells were restimulated in the absence, and FIG. 5B refers to an experiment in which effector cells were restimulated in the presence of IL2. As is evident from FIG. 5A, immunization with hsp65-NP.B fusion protein results in a dramatic stimulation of specific CTL activity directed against target cells displaying the NP.B peptide, ranging from about 20 to 40% lysis of target cells at an effector:target cell ratio of 100. Essentially no specific lysis was observed with effector cells from DPBS- "immunized" animals. Also, no significant lysis of E7-peptide-pulsed cells was evident. In the experiment with effector cells restimulated in the presence of IL2, even higher levels of target cells lysis were observed with effector cells from hsp65-NP.B of fusion protein-immunized mice. Levels ranged from about 25 to 60% at an effector:target cell ratio of 100, depending on the fusion protein dose. These values greatly exceed the 10–15% lysis observed with effector cells from DPBS-injected mice. Again, no significant (greater than that observed with effector cells from DPBS-"immunized" mice), specific layers lysis of E7 peptide-pulsed target cells was observed.

Figure 6A:
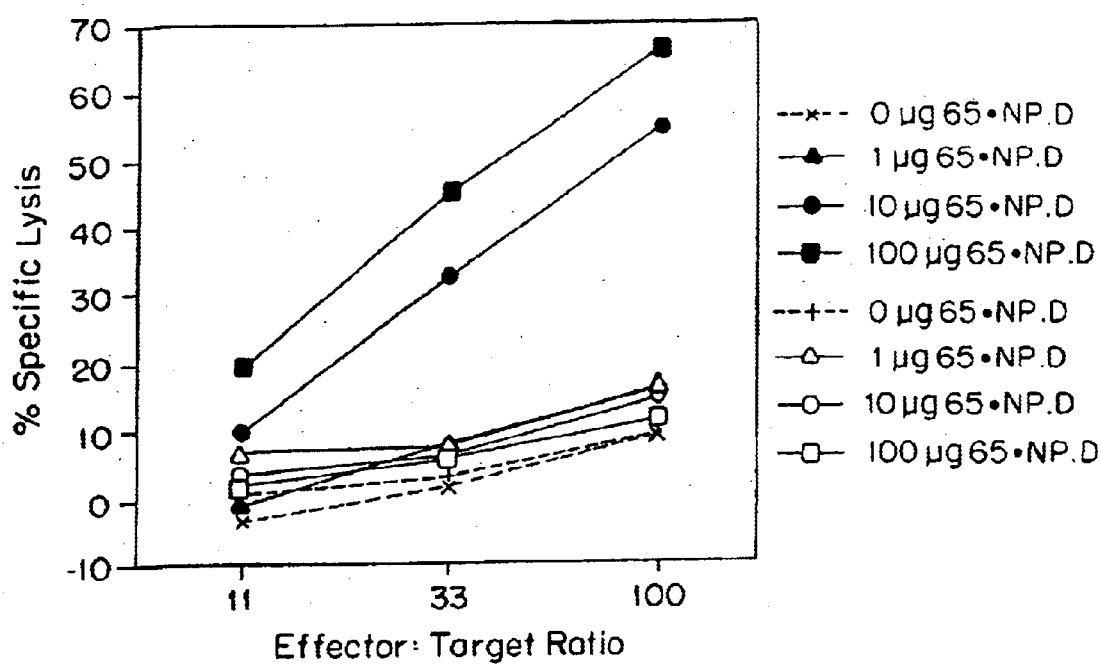
FIGS. 6A–6B are graphs of effector:target ratio versus % specific cell lysis demonstrating a CTL response in mice to the hsp-NP fusion protein, hsp65-NP.D, wherein the effector cells were restimulated in the absence of IL-2 (FIG. 6A) and in the presence of IL-2 (FIG. 5B).
Figure 6B:
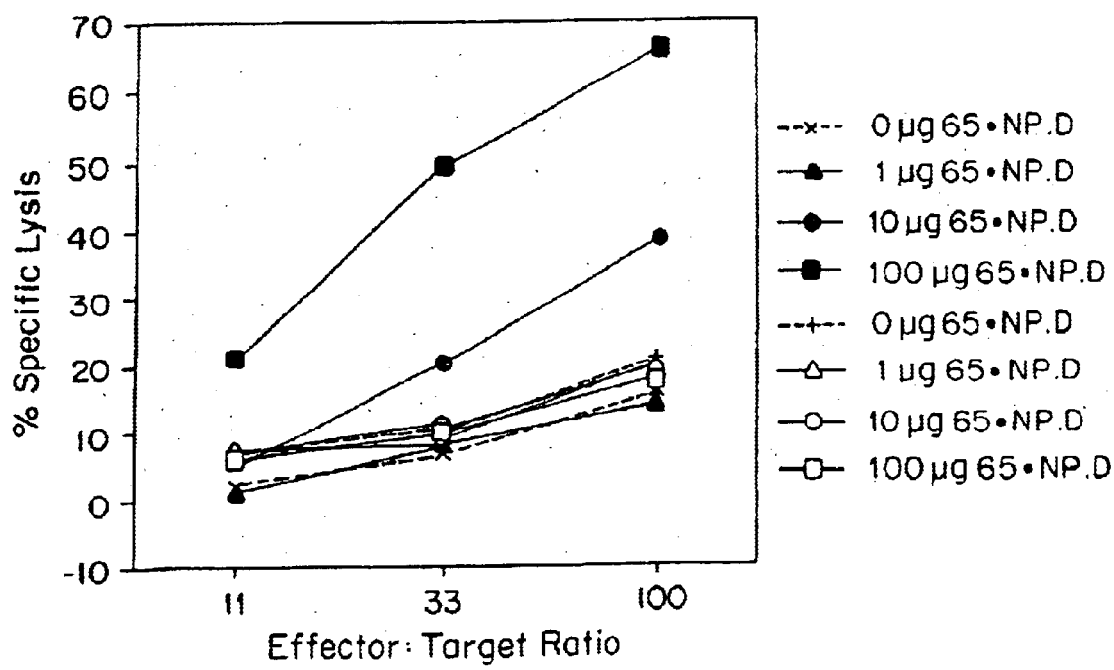

Results of experiments with hsp65-NP.D fusion protein (labeled 65-NP.D) are shown in FIGS. 6A–6B. Generally, these results are similar to those obtained in experiments with the hsp65-NP.B fusion protein. Note that, unlike in the previous experiment with hsp65-NP.B, a clear dependence on the dose of hsp65-NP.D peptide used in immunization was observed in this experiment. Together, these experiments, using hsp65-NP fusion proteins as examples, demonstrate that immunization with an hsp-foreign peptide/polypeptide fusion protein results in a drastic stimulation of CTL activity directed against appropriate target cells displaying epitopes contained in the foreign peptide/polypeptide fusion partner.

Example 5

CTL Responses to an hsp-P1A Fusion Protein

Using procedures similar to those used in the preceding example, a plasmid was constructed that permitted expression *E. coli* of a fusion gene containing the complete coding sequence of M. tuberculosis stress protein hsp71 and, added to the carboxy end of the hsp71 sequence, four tandemly arranged copies of a synthetic sequence encoding the minimal CTL epitope of tumor-associated antigen P1a (LPYLGWLVP (SEQ ID NO: 7); this sequence is referred to as P1a in this example). Hsp71-P1A fusion protein (referred to as 71-P1A(4) in FIGS. 7A, 7B, 8A, 8B and 9) was expressed and purified using standard biochemical methods similar to those used in the preceding example.

Figure 7A:
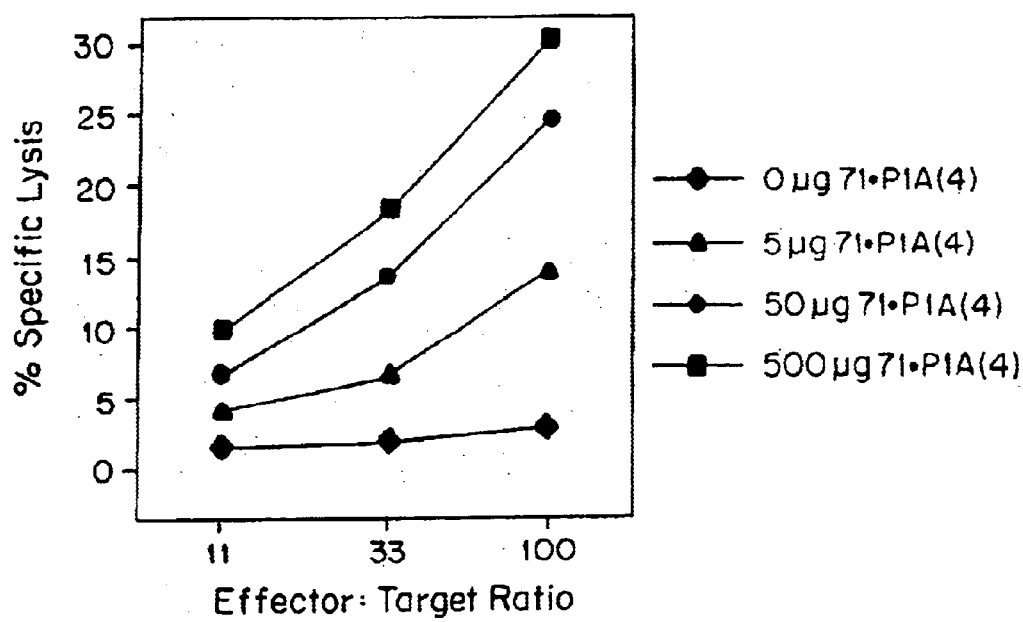
FIGS. 7A–7B are graphs of effector:target ratio versus % specific cell lysis demonstrating a CTL response in BALB/c mice immunized with an hsp-P1A fusion protein.
Figure 7B:
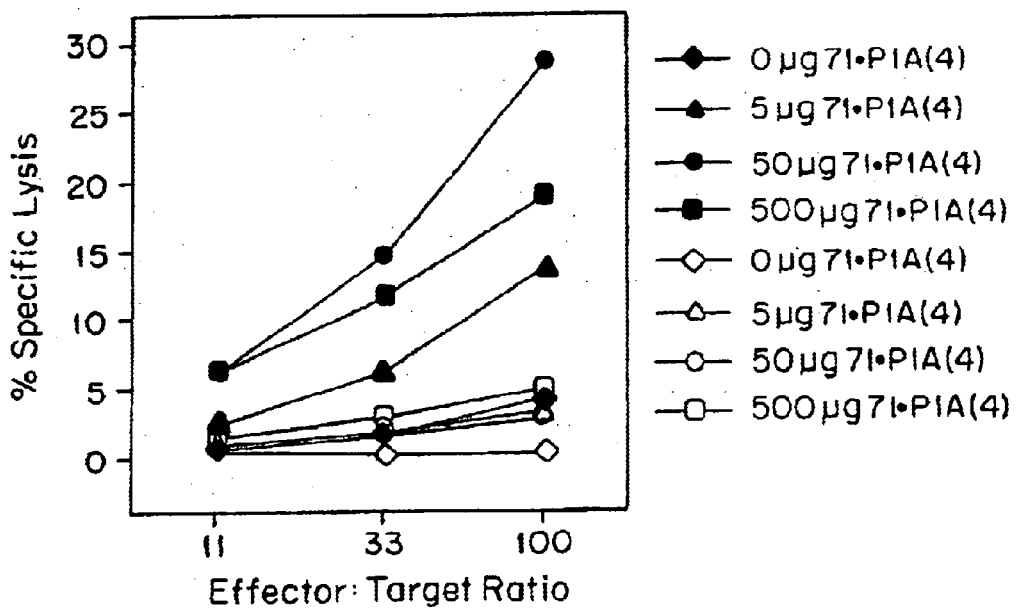
Figure 8A:
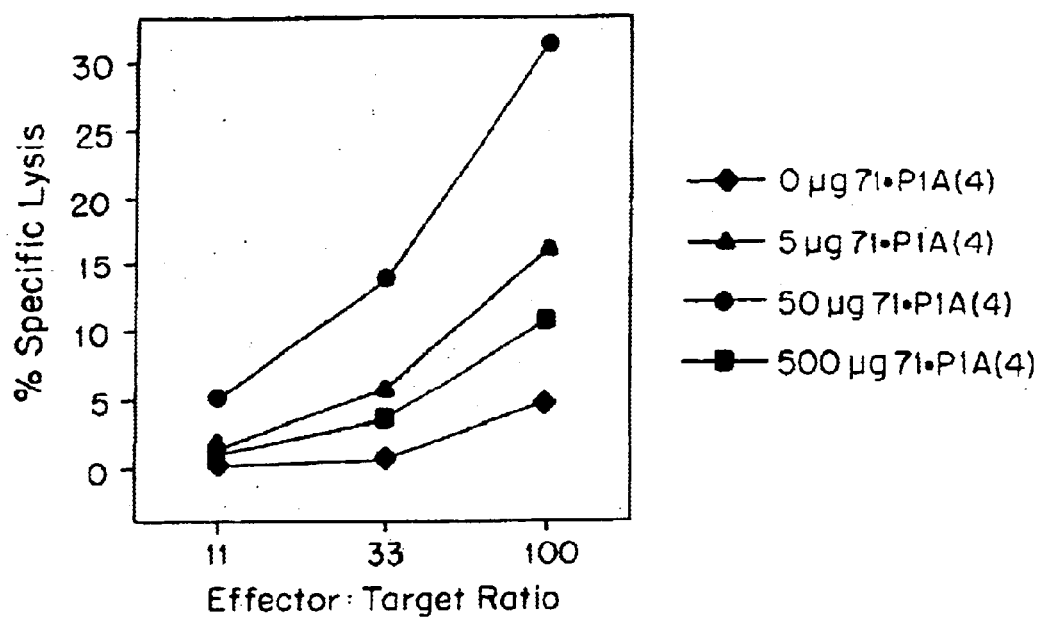
FIGS. 8A–8B are graphs of effector:target ratio versus % specific cell lysis demonstrating a CTL response in DBA/2 ($H-2^d$) mice immunized with an hsp-P1A fusion protein.
Figure 8B:
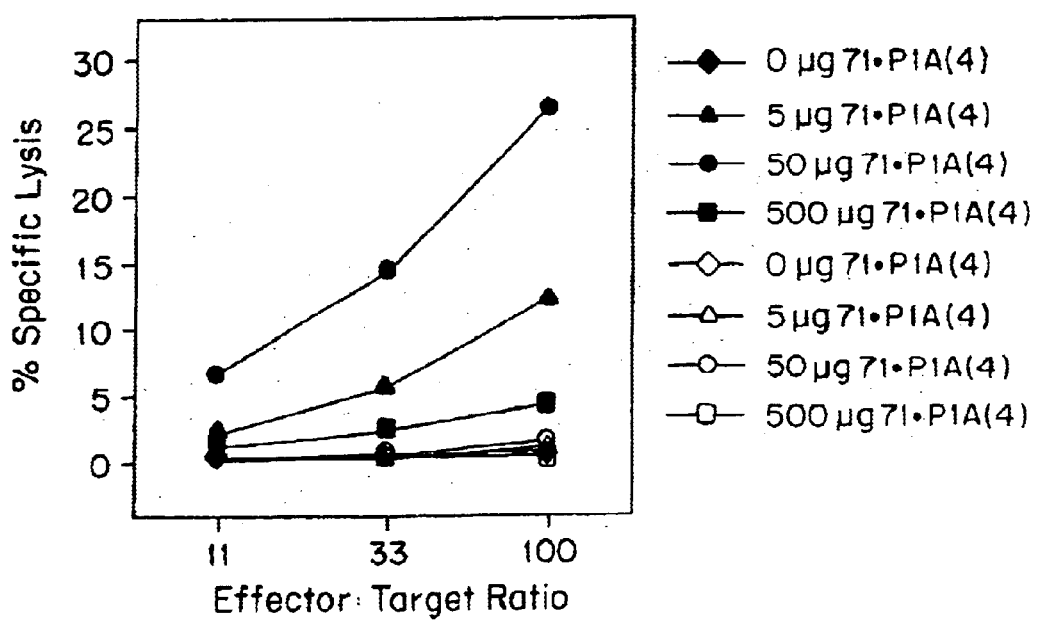

BALB/c or DBA/2 (H-2$^d$) mice were anesthetized by intraperitoneal injection of ketamine hydrochloride. The mice were then immunized subcutaneously in the nape of the neck with 0, 5, 50 or 500 μg of hsp71-P1A fusion protein. The immunogen was administered in DPBS without adjuvant. One week later, single cell suspensions form four pooled spleens per group were prepared and restimulated in vitro for 7 days with synthetic peptide CKKKLPYLGWLVP (SEQ ID NO: 8) (1 μM). Note that the CKKK residues were added to enhance the aqueous solubility of the P1A nonamer. Restimulated effector cells were then cultured for 4–5 hours with $^{51}$Cr-labelled target cells. Targets were cells of the P1A antigen-expressing clone P1 (H-2$^d$) of the P815 mastocytoma, or, alternatively, L1210 cells (H-2$^J$) pulsed with (CKKK) P1A, as control targets, unpulsed L1210 cells at effector:target ratios of 100, 33 or 11:1. Specific lysis of target cells were determined as described in Example 2. The results of these experiments are represented in FIGS. 7A–7B (BALB/c mice) and 8A–8B (DBA/2 mice). Background lysis in these experiments was less that 5%, as indicated by the lytic activity observed against irrelevant target cells (unpulsed L1210 cells). Restimulated cells from unimmunized mice (0 μg) exhibited no lytic activity against either P1 target cells (FIGS. 7A, 8A) or CKKK (P1A)-pulsed L1210 cells (FIGS. 7B, 8B). Cells from mice immunized with as little as 5 μg of hsp71-P1A fusion protein exhibited measurable lytic activity, with the maximal response seen in cells from mice immunized with 50–500 μg.

Example 6

Tumor Challenge of Mice Immunized with hsp71-P1A Fusion Protein

Figure 9:
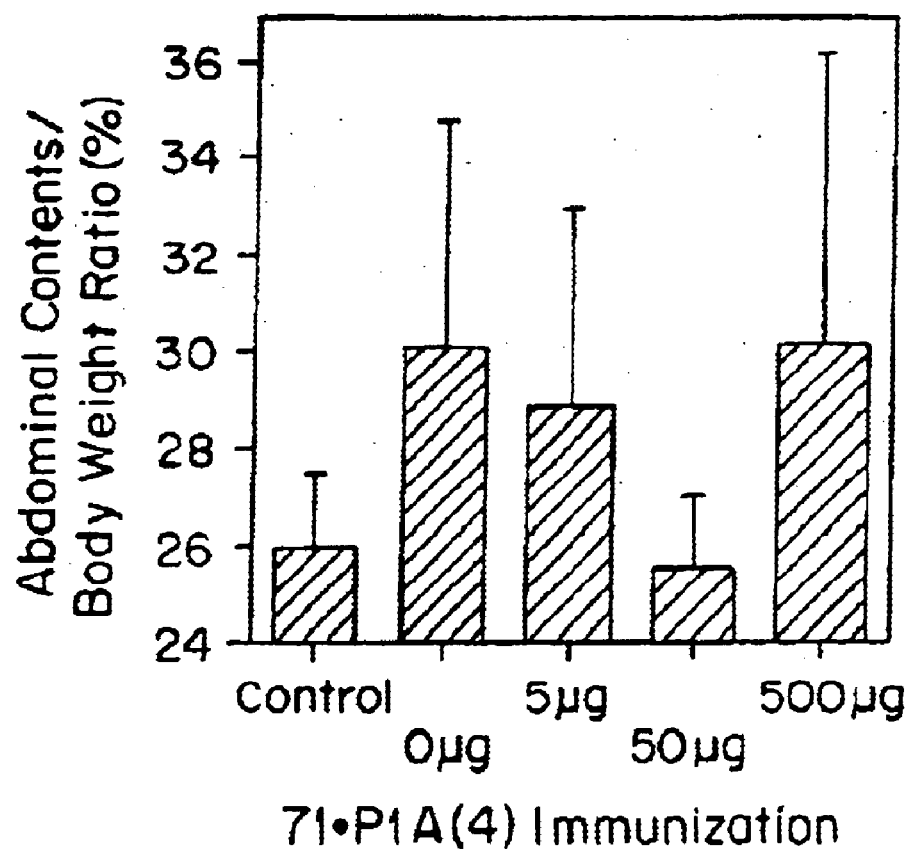
FIG. 9 is a bar graph demonstrating that immunization with the hsp-tumor-associated antigen, hsp71-P1A, results in stimulation of CTL activity directed against cells displaying relevant MHC class I-restricted epitopes.

Mice were immunized as in the preceding example, except that three injections were given at intervals of two weeks. Two weeks after the final injection, the mice were challenged by intraperitoneal injection of 1000 viable P1 tumour cells. After 26 days, the mice were euthanized, weighed, and the entire mass of abdominal contents was dissected and weighed. The results of this experiment are shown in FIG. 9. It was observed that in mice given three 50 μg immunizations with hsp71-P1A fusion protein, the mass of the abdominal contents, as expressed as a percentage of the total body weight, was significantly less than that found in unimmunized mice (0 μg, P<0.03), and similar to that observed in mice which were not injected with tumor cells (control).

Together, the experiments in Examples 5 and 6 demonstrate that immunization with hsp-tumor-associated antigen, using hsp71-P1A as the example, results in substantial stimulation of CTL activity directed against cells displaying irrelevant MHC class I-restricted epitopes. Further, such immunization leads to the expression of a relevant effector function, namely immunity against challenge with a tumor expressing the antigen immunized against.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A fusion protein comprising an antigen of an influenza virus and a stress protein, wherein the antigen of the influenza virus is nucleoprotein, neuraminidase, M1, M2, PB1, PB2, or PA, the stress protein is an Hsp 100–200, an Hsp100, an Hsp90, Lon, an Hsp70, an Hsp60, TF55, an Hsp40, an FKBP, a cyclophillin, an Hsp20–30. ClpP, GrpE, Hsp10, ubiquitin, calnexin, or a protein disulfide isomerase, and the fusion protein induces an immune response against the antigen in a mammal to whom the fusion protein is administered.

2. The fusion protein of claim 1, wherein the antigen of the influenza virus is nucleoprotein.

3. The fusion protein of claim 1, wherein the antigen includes a CTL epitope.

4. The fusion protein of claim 3, wherein the CTL epitope is a class I-restricted T cell epitope.

5. The fusion protein of claim 3, wherein the CTL epitope is a class II-restricted T cell epitope.

6. A composition comprising the fusion protein of claim 1 and a pharmaceutically acceptable excipient, carrier, diluent, or vehicle.

7. A method of inducing an immune response against an antigen of an influenza virus, the method comprising administering the fusion protein of claim 2 to a vertebrate in an amount effective to induce an immune response against the antigen.

8. The method of claim 7, wherein the fusion protein is administered in combination with a pharmaceutically acceptable excipient, carrier, diluent, or vehicle.

9. The method of claim 7, wherein the immune response is a cell mediated immune response.

10. The method of claim 7, wherein the cell mediated immune respone is a cell mediated cytolytic immune response.

11. The method of claim 9, wherein the cell mediated immune response is a class I-restricted T cell response.

12. The method of claim 9, wherein the cell mediated immune response is a class II-restricted T cell response.

13. The fusion protein of claim 1, wherein the immune response is a cell mediated immune response.

14. The fusion protein of claim 13, wherein the cell mediated immune response is a cell mediated cytolytic immune response.

15. The fusion protein of claim 13, wherein the cell mediated immune response is a class I-restricted T cell response.

16. The fusion protein of claim 13, wherein the cell mediated immune response is a class II-restricted T cell response.

17. The fusion protein of claim 1, wherein the stress protein is a mammalian stress protein.

18. The fusion protein of claim 17, wherein the mammalian stress protein is a human stress protein.

19. The fusion protein of claim 1, wherein the stress protein is an Hsp100–200.

20. The fusion protein of claim 19, wherein the Hsp100–200 is a Grp 170.

21. The fusion protein of claim 1, wherein the stress protein is an Hsp100.

22. The fusion protein of claim 21, wherein the Hsp100 is a mammalian Hsp110, a yeast Hsp104, or a clpA, ClpB, clpC, clpX or clpY stress protein.

23. The fusion protein of claim 1, wherein the stress protein is an Hsp90.

24. The fusion protein of claim 23, wherein the Hsp90.

25. The fusion protein of claim 1, wherein the stress protein is Lon.

26. The fusion protein of claim 1, wherein the stress protein is an Hsp70.

27. The fusion protein of claim 26, wherein the Hsp70 is a mammalian Hsp72 or Hsp73.

28. The fusion protein of claim 1, wherein the stress protein is an Hsp60.

29. The fusion protein of claim 1, wherein the stress protein is a TF55.

30. The fusion protein of claim 1, wherein the stress protein is an Hsp40.

31. The fusion protein of claim 1, wherein the stress protein is an FKBP.

32. The fusion protein of claim 31, wherein the KFBP is FKBP12, FKBP13, FKBP25, FKBP59, Fprl, or Nepl.

33. The fusion protein of claim 1, wherein the stress protein is a cyclophilin.

34. The fusion protein of claim 33, wherein the cyclophilin is cyclophilin A, cyclophilin B, or cyclophilin C.

35. The fusion protein of claim 1, wherein the stress protein is an Hsp20–30.

36. The fusion protein of claim 35, wherein the Hsp20–30 is a Tcpl, TriC, or thermosome.

37. The fusion protein of claim 1, wherein the stress protein is a ClpP.

38. The fusion protein of claim 1, wherein the stress protein is a GrpE.

39. The fusion protein of claim 1, wherein the stress protein is an Hsp10.

40. The fusion protein of claim 39, wherein the Hsp10 is GroEs or Cpn10.

41. The fusion protein of claim 1, wherein the stress protein is a ubiquitin, calnexin, or protein disulfide isomerase.

42. The fusion protein of claim 1, wherein the antigen of the influenza virus is neuraminidase.

43. The fusion protein of claim 1, wherein the antigen of the influenza virus of M1 or M2.

44. The fusion protein of claim 1, wherein the antigen of the influenza virus is PB1, PB2, or PA.

45. A fusion protein comprising an amino acid squence encoded by plasmid pET65MP/NP-B or plasmid pET65MP/NP-D.

46. A method of inducing an immune response against an antigen of the influenza virus, the method comprising administering the fusion protein of claim 45 to a vertebrate in an amount effective to induce an immune response against the antigen.

47. The method of claim 46, wherein the fusion protein is administered in combination with a pharmaceutically acceptable excipient, carrier, diluent, or vehicle.

48. A fusion protein comprising an antigen of an influenza virus, and a bacterial stress protein, wherein the antigen of the influenza virus is nucleoprotein, neuraminidase, M1, M2, PB1, PB2, or PA and the fusion protein induces an immune response against the antigen in a mammal to whom the fusion protein is administered.

49. The fusion protein of claim 48, wherein the bacterial stress protein is a mycobacterial stress protein.

50. The fusion protein of claim 49, wherein the stress protein is hsp65.

51. The fusion protein of claim 49, wherein the stress protein is hsp71.

52. The fusion protein of claim 48, wherein the mycobacterial stress protein is stress protein of *Mycobacterium leprae, Mycobacterium tuberculosis*, or *Mycobacterium bovis*.

53. The fusion protein of claim 48, wherein the bacterial stress protein is an enterobacterial stress protein.

54. The fusion protein of claim 48, wherein the bacterial stress protein is an *E. Coli* stress protein.

55. The fusion protein of claim 48, wherein the bacterial stress protein is an Hsp90, Hsp70, Hsp40, or Hsp10.

56. The fusion of claim 55, wherein the Hsp90 is an HtpG.

57. The fusion protein of claim 55, wherein the Hsp70 is a DnaK.

58. The fusion protein of claim 55, wherein the Hsp60 is an hsp65 is an hsp65 or GroEL.

59. The fusion protein of claim 55, wherein the Hsp40 is a DnaJ.

60. The fusion protein of claim 55, wherein the Hsp10 is a GroES.

* * * * *